(12) United States Patent
Park et al.

(10) Patent No.: US 12,136,483 B2
(45) Date of Patent: Nov. 5, 2024

(54) APPARATUS AND METHOD FOR PROCESSING MEDICAL IMAGE USING PREDICTED METADATA

(71) Applicant: Lunit Inc., Seoul (KR)

(72) Inventors: Jong Chan Park, Seoul (KR); Dong Geun Yoo, Seoul (KR); Ki Hyun You, Seoul (KR); Hyeon Seob Nam, Seoul (KR); Hyun Jae Lee, Seoul (KR); Sang Hyup Lee, Seoul (KR)

(73) Assignee: LUNIT INC., Seoul (KR)

( * ) Notice: Subject to any disclaimer, the term of this patent is extended or adjusted under 35 U.S.C. 154(b) by 0 days.

(21) Appl. No.: 18/627,705

(22) Filed: Apr. 5, 2024

(65) Prior Publication Data
US 2024/0249824 A1 Jul. 25, 2024

Related U.S. Application Data

(63) Continuation of application No. 17/426,336, filed as application No. PCT/KR2020/006712 on May 22, 2020, now Pat. No. 11,978,548.

(30) Foreign Application Priority Data

May 22, 2019 (KR) .......................... 10-2019-0059860

(51) Int. Cl.
| | | |
|---|---|---|
| *G16H 30/20* | (2018.01) | |
| *G06T 7/00* | (2017.01) | |
| *G06V 30/166* | (2022.01) | |
| *G16H 30/40* | (2018.01) | |

(52) U.S. Cl.
CPC ........... *G16H 30/20* (2018.01); *G06T 7/0012* (2013.01); *G06V 30/166* (2022.01); *G16H 30/40* (2018.01); *G06T 2207/30004* (2013.01)

(58) Field of Classification Search
CPC ...... G16H 30/20; G16H 30/40; G06T 7/0012; G06T 2207/30004; G06V 30/166
See application file for complete search history.

(56) References Cited

U.S. PATENT DOCUMENTS

| | | | |
|---|---|---|---|
| 10,222,942 B1 | 3/2019 | Zeiler et al. | |
| 2019/0392547 A1* | 12/2019 | Katouzian | ............. G06V 20/62 |
| 2020/0005088 A1 | 1/2020 | Joy | |

OTHER PUBLICATIONS

USPTO, Notice of Allowance of U.S. Appl. No. 17/685,740 dated Jun. 4, 2024, total 92 pages.
Lituiev, Dmytro S. et al., "Automatic Labeling of Special Diagnostic Mammography Views from Images and DICOM Headers", Journal of Digital Imaging, vol. 32, No. 2, Nov. 21, 2018, p. 228-233, XP036754540.

(Continued)

*Primary Examiner* — Casey L Kretzer
(74) *Attorney, Agent, or Firm* — LEX IP MEISTER, PLLC

(57) ABSTRACT

The present disclosure relates to a medical image analysis method using a processor and a memory which are hardware. The method includes generating predicted second metadata for a medical image by using a prediction model, and determining a processing method of the medical image based on one of first metadata stored corresponding to the medical image and the second metadata.

14 Claims, 12 Drawing Sheets

(56) References Cited

OTHER PUBLICATIONS

Filice, Ross W. et al., "Effectiveness of Deep Learning Algorithms to Determine Laterality in Radiographs", Journal of Digital Imaging, vol. 32, No. 4, May 7, 2019, p. 656-664, XP036855008.
Ivica Dimitrovski et al., "Hierarchical annotation of medical images", Pateern Recognition, vol. 44, No. 10-11, p. 2436-2449, (Mar. 29, 2011).

* cited by examiner

FIG. 5

| | 511 | 512 | 513 |
|---|---|---|---|
| CT image | | | |
| Window graph | 521 | 522 | 523 |
| Window center | a | a | d |
| Window width | b | c | c |

FIG. 14

Example of case where abnormality detection machine learning model is not applied 1410 — 1) len(dcm.ViewCodeSequence[0].ViewModifierCodeSequence) !=0

1420 — 2) dcm.PresentationIntentType == 'FOR PRCESSING'

1430 — 3) dcm.ViewPosition not in ['CC', 'MLO' ]

1440 — 4) float(dcm.EstimatedRadiographicMagnificationFactor) > (1.0)

1450 — 5) dcm.Laterality == 'L' and dcm.ImageOrientationPatient[1] == 1

1460 — 6) dcm.Laterality == 'R' and dcm.ImageOrientationPatient[1] == -1

1470 — 7) dcm.BreastImplantPresent == 'YES'

FIG. 15

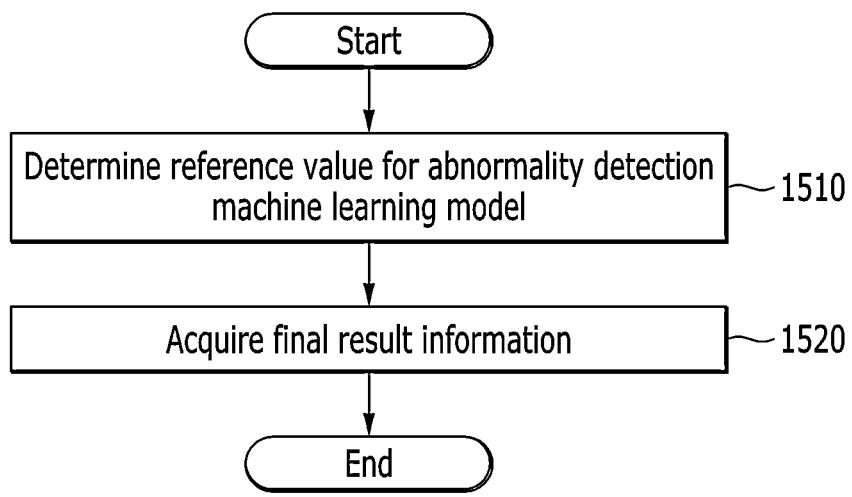

APPARATUS AND METHOD FOR PROCESSING MEDICAL IMAGE USING PREDICTED METADATA

CROSS-REFERENCE TO RELATED APPLICATIONS

This application is a continuation application of U.S. application Ser. No. 17/426,336 filed on Jul. 28, 2021, a national phase entry under 35 U.S.C. § 371 of International Application No. PCT/KR2020/006712 filed on May 22, 2020, which claims priority from Korean Patent Application No. 10-2019-0059860 filed on May 22, 2019, all of which are incorporated by reference.

BACKGROUND

(a) Field

The present disclosure relates to an apparatus and method that predicts metadata by applying a machine learning model to a medical image and processes the medical image using the predicted metadata.

(b) Description of the Related Art

According to digital imaging and communications and medicine (DICOM), being a data standard for medical images, DICOM data largely contain two types of information. One is a photographed original medical image (raw pixel array), and the other is metadata recorded on a DICOM header.

During medical image analysis, values recorded on the DICOM header are used first. For example, a medical worker determines whether a medical image corresponds to a body part of a patient to be read by identifying a value of "BodyPartExamined" attribute of the DICOM header and then interprets the medical image. In addition, the medical worker may normalize original images obtained from diverse environments by using "Window Center/Width" attribute of the DICOM header.

Each hospital has a different protocol for metadata of the medical images stored on the DICOM header, and each radiologist may input a different subjective value. In addition, the metadata of the DICOM header may vary depending on the photographing equipment. In some cases, the DICOM header may not have any value, have an incorrect value, or have values stored according to different criteria. In this case, the medical worker cannot interpret medical images or may misinterpret them. In addition, normalized medical images are required for machine learning of medical images. However, machine learning cannot be performed properly on medical images if the metadata are stored according to different criteria.

SUMMARY

A medical image analysis method according to an embodiment of the present disclosure includes generating predicted second metadata for a medical image by using a prediction model, and determining a processing method of the medical image based on one of first metadata stored corresponding to the medical image and the second metadata.

In a medical image analysis method according to an embodiment, determining the processing method of the medical image includes selecting one of the first metadata and the second metadata based on reliability of the second metadata, and determining the processing method of the medical image based on the selected metadata.

In a medical image analysis method according to an embodiment, selecting one of the first metadata and the second metadata includes selecting the second metadata when the reliability of the second metadata is greater than or equal to a criterion, and selecting the first metadata when the reliability of the second metadata is less than the criterion.

In a medical image analysis method according to an embodiment, determining the processing method of the medical image includes determining the processing method of the medical image based on the second metadata when the first metadata does not contain information on at least one item related to the processing method.

In a medical image analysis method according to an embodiment, determining the processing method of the medical image includes applying the medical image to an abnormality detection machine learning model when the selected metadata satisfies a predetermined condition.

In a medical image analysis method according to an embodiment, determining the processing method of the medical image includes not applying the medical image to an abnormality detection machine learning model when information related to at least one item contained in the selected metadata does not satisfy a predetermined condition.

In a medical image analysis method according to an embodiment, determining the processing method of the medical image includes determining a reference value related to determination in an abnormality detection machine learning model based on the selected metadata, acquiring result information by applying the medical image to the abnormality detection machine learning model, and acquiring final result information by comparing the reference value with the result information.

In a medical image analysis method according to an embodiment, determining the processing method of the medical image includes selecting an abnormality detection machine learning model corresponding to the selected metadata from multiple abnormality detection machine learning models, and applying the medical image to the selected abnormality detection machine learning model.

In a medical image analysis method according to an embodiment, the information related to at least one item contained in the selected metadata includes at least one of information on whether spot compression was used, information on presentation intent type, information on a view, magnification information, information related to image rotation, information on existence of an artifact, age information of a patient, and information on a body part of a patient.

In a medical image analysis method according to an embodiment, the prediction model is a machine learning model for predicting metadata corresponding to the medical image from the medical image.

In a medical image analysis method according to an embodiment, at least one of the first metadata and the second metadata includes at least one of information related to an object included in the medical image, information on an imaging environment of the medical image, information on a type of the medical image, and information related to a display method of the medical image.

A medical image analysis apparatus according the present disclosure includes a processor and a memory. Based on instructions stored on the memory, the processor generates second metadata for a medical image by using a prediction model, and determines a processing method of the medical image based on one of first metadata stored corresponding to the medical image and the second metadata.

In a medical image analysis apparatus according the present disclosure, based on instructions stored on the memory, the processor selects one of the first metadata and the second metadata based on reliability of the second metadata, and determines the processing method of the medical image based on the selected metadata.

In a medical image analysis apparatus according the present disclosure, based on instructions stored on the memory, the processor selects the second metadata when the reliability of the second metadata is greater than or equal to a criterion, and selects the first metadata when the reliability of the second metadata is less than the criterion.

In a medical image analysis apparatus according the present disclosure, based on instructions stored on the memory, the processor determines the processing method of the medical image based on the second metadata when the first metadata does not contain information on at least one item related to the processing method.

In a medical image analysis apparatus according the present disclosure, based on instructions stored on the memory, the processor applies the medical image to an abnormality detection machine learning model when the selected metadata satisfies a predetermined condition.

In a medical image analysis apparatus according the present disclosure, based on instructions stored on the memory, the processor does not apply the medical image to an abnormality detection machine learning model when the information related to at least one item included in the selected metadata does not satisfy a predetermined condition.

In a medical image analysis apparatus according the present disclosure, based on instructions stored on the memory, the processor determines a reference value related to determination in an abnormality detection machine learning model based on the selected metadata, acquires result information by applying the medical image to the abnormality detection machine learning model, and acquires final result information by comparing the reference value with the result information.

In a medical image analysis apparatus according the present disclosure, based on instructions stored on the memory, the processor selects an abnormality detection machine learning model corresponding to the selected metadata from multiple abnormality detection machine learning models, and applies the medical image to the selected abnormality detection machine learning model.

In a medical image analysis apparatus according the present disclosure, the information related to at least one item contained in the selected metadata includes at least one of information on whether spot compression was used, information on presentation intent type, information on a view, magnification information, information related to image rotation, information on existence of an artifact, age information of a patient, and information on a body part of a patient.

The prediction model of the medical image analysis apparatus according to an embodiment of the present disclosure is a machine learning model for predicting metadata corresponding to a medical image from the medical image.

In a medical image analysis apparatus according the present disclosure, at least one of the first metadata and the second metadata of the medical image analysis apparatus according to an embodiment of the present disclosure includes at least one of information related to an object included in the medical image, information on a imaging environment of the medical image, information on a type of the medical image, and information related to a display method of the medical image.

In addition, a program to implement the medical image analysis method as described above may be recorded on a computer-readable recording medium.

BRIEF DESCRIPTION OF THE DRAWINGS

FIG. 5 shows CT information based on window center information and window width information according to an embodiment of the present disclosure.

FIG. 14 is a diagram showing a condition on which a medical image is not applied to an abnormality detection machine learning model according to an embodiment of the present disclosure.

FIG. 15 is a flowchart illustrating an operation of a medical image analysis apparatus according to an embodiment of the present disclosure.

DETAILED DESCRIPTION OF THE EMBODIMENTS

Figure 1:
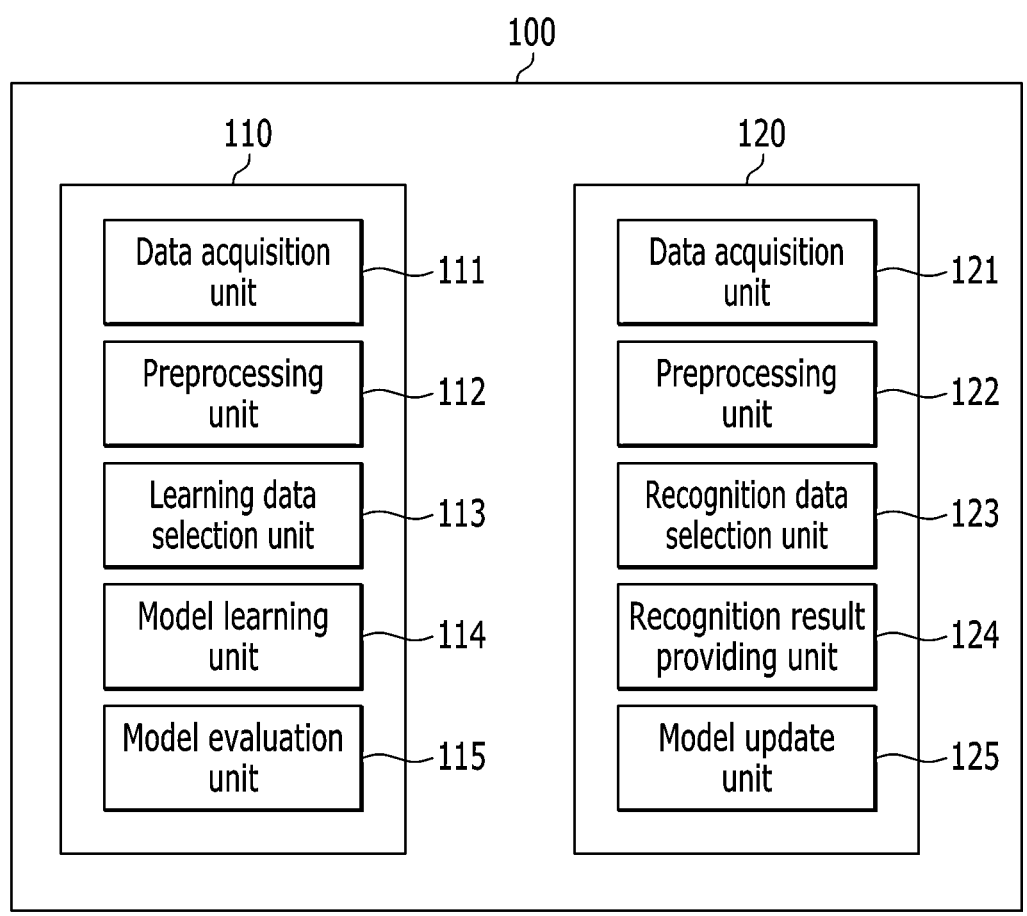
FIG. 1 is a block diagram of a medical image analysis apparatus 100 according to an embodiment of the present disclosure.

Merits and characteristics of embodiments disclosed and methods of achieving them would be clarified by referring to the embodiments described below with attached drawings. However, this disclosure is not limited to the embodiments disclosed below and can be embodied into diverse forms. These embodiments are simply provided to make this disclosure complete and to completely inform the scope of this invention to persons with common knowledge in the art of this disclosure.

Terms used in this specification will be explained briefly, disclosed embodiments will be explained in detail.

The terms used in this specification are general terms that are used widely, selected in consideration of functions of this disclosure. These terms can be changed according to intention of engineers of in the art, precedents, appearance of new technologies, and the like. In addition, certain terms were selected arbitrarily by the applicant, for which case meanings of such terms will be explained in detail. Therefore, the terms used in this disclosure must be defined based on their definitions and overall application in this disclosure instead of their names.

Unless clearly specified to be singular, singular expressions used in this specification also include plural expressions. In addition, unless clearly specified to be plural, plural expressions shall include singular expressions.

Throughout the specification, when a part is referred to "include" a certain element, it means that it may further include other elements rather than exclude other elements, unless specifically indicates otherwise.

In addition, term "unit" used in this specification refers to a software or hardware component. A "unit" plays certain roles, but it is not limited to software or hardware. A "unit" can be configured to be included in an addressable storage medium or to invoke one or more processors. Therefore, for example, a "unit" includes processes, functions, attributes, procedures, subroutines, program code segments, drivers, firmware, microcode, circuit, data, database, data structures, tables, arrays, variables, and components such as software components, object oriented software components, class components and task components. Functions provided within the components and "units" can be combined into smaller number of components and "units" or further divided into sub-components and sub-"units".

According to an embodiment of the present disclosure, a "unit" can be implemented with a processor and a memory. The term "processor" should be interpreted broadly to include a general-purpose processor, a central processing unit (CPU), a microprocessor, a digital signal processor (DSP), a controller, a microcontroller, a state machine, and the like. In some environments, the "processor" may refer to an application specific integrated circuit (ASIC), a programmable logic device (PLD), a field programmable gate array (FPGA), and the like. The term "processor" may for example, also refer to a combination of a DSP and a microprocessor, a combination of multiple microprocessors, a combination of one or more microprocessors combined with a DSP core, or a combination of processing devices such as a combination of any other such components.

The term "memory" should be interpreted broadly to include any electronic component capable of storing electronic information. The term "memory" may also refer to various types of processor-readable medium such as a random-access memory (RAM), a read-only memory (ROM), a non-volatile random-access memory (NVRAM), a programmable read-only memory (PROM), an erasable programmable read-only memory (EPROM), an electrically erasable pROM (EEPROM), a flash memory, a magnetic or optical data storage device, registers, and the like. If a processor can read information from a memory and/or record information on a memory, the memory is referred to be in an electronic communication state with the processor. A memory integrated in a processor is in an electronic communication state with the processor.

Hereinafter, exemplary embodiments will be described in detail with reference to the accompanying drawings so that those skilled in the art may easily implement the embodiments. In order to clearly explain the present disclosure in the drawings, portions not related to the description will be omitted.

FIG. 1 is a block diagram of a medical image analysis apparatus 100 according to an embodiment of the present disclosure.

Referring to FIG. 1, the medical image analysis apparatus 100 according to an embodiment may include a data learning unit 110 and a data recognition unit 120. The medical image analysis apparatus 100 as above-described may include a processor and a memory.

The data learning unit 110 can train a machine learning model to perform a target task by using a data set. The data learning unit 110 can receive the data set and label information related to the target task. The data learning unit 110 can obtain a machine learning model by performing machine learning on a relationship between the data set and the label information. In an embodiment, the machine learning model obtained by the data learning unit 110 may be a model to generate label information using a data set.

The data recognition unit 120 can store the machine learning model of the data learning unit 110. The data recognition unit 120 can output label information predicted by applying the machine learning model to input data. In addition, the data recognition unit 120 can use the input data, the label information, and a result output from the machine learning model for updating the machine learning model.

At least one of the data learning unit 110 and the data recognition unit 120 may be manufactured as at least one hardware chip and mounted on an electronic device. For example, at least one of the data learning unit 110 and the data recognition unit 120 may be manufactured in the form of a dedicated hardware chip for artificial intelligence (AI) or an existing general-purpose processor (e.g., CPU or application processor), or as part of a graphics-only processor (e.g., GPU) to be mounted on various electronic devices.

In addition, the data learning unit 110 and the data recognition unit 120 may be mounted on separate electronic devices, respectively. For example, one of the data learning unit 110 and the data recognition unit 120 may be included in an electronic device and the other may be included in a server. In addition, the data learning unit 110 and the data recognition unit 120 may provide information on the machine learning model built by the data learning unit 110 to the data recognition unit 120 through wire or wireless communication. The data input into the data recognition unit 120 may be provided to the data learning unit 110 as additional learning data.

Meanwhile, at least one of the data learning unit 110 and the data recognition unit 120 may be implemented as a software module. When at least one of the data learning unit 110 and data recognition unit 120 is implemented as a software module (or a program module including instructions), the software module may be stored on a memory or a non-transitory computer readable media. In addition, in this case, at least one software module may be provided by an operating system (OS) or a predetermined application. Alternatively, some of at least one software module may be provided by the operating system (OS), and the others may be provided by the predetermined application.

The data learning unit 110 according to an embodiment of the present disclosure may include a data acquisition unit 111, a preprocessing unit 112, a learning data selection unit 113, a model learning unit 114, and a model evaluation unit 115.

The data acquisition unit 111 can acquire data required for machine learning. Since a large volume of data is required for learning, the data acquisition unit 111 may receive a data set including multiple data.

Label information may be assigned to each of the multiple data. The label information may be ground truth information that explains each of multiple data. The label information may be information to be derived by a target task. The label information may be acquired from a user input, a memory, or the result of the machine learning model. For example, if the target task is to determine whether a specific object exists in an image, the multiple data would be data of multiple images and the label information would be whether the specific object exists in each of the multiple images.

The preprocessing unit 112 may preprocess the acquired data so that the received data can be used for machine learning. The preprocessing unit 112 may process the acquired data set in a predetermined format to be used by the model learning unit 114 that will be described later.

The learning data selection unit 113 can select data required for learning from the pre-processed data. The selected data may be provided to the model learning unit 114. The learning data selection unit 113 can select data necessary for learning from the pre-processed data according to a predetermined criterion. In addition, the learning data selection unit 113 may also select data according to a criterion predetermined by learning of the model learning unit 114 that will be described later.

The model learning unit 114 can learn a criterion for which label information will be output based on the data set. In addition, the model learning unit 114 can perform machine learning by using the data set and the label information for the data set as learning data. In addition, the model learning unit 114 may perform machine learning by additionally using a previously acquired machine learning model. In this case, the previously acquired machine learning model may be a model constructed in advance. For example, the machine learning model may be a model constructed in advance by receiving basic learning data as input.

The machine learning model may be constructed in consideration of application field of the learning model, purpose of learning, computer performance of a device, and the like. The machine learning model may be, for example, a model based on a neural network. For example, models such as a deep neural network (DNN), a recurrent neural network (RNN), a long short-term memory model (LSTM), a bidirectional recurrent deep neural network (BRDNN), and a convolutional neural network (CNN) may be used as the machine learning model. However, the machine learning model is not limited thereto.

According to various embodiments, when there are multiple pre-constructed machine learning models, the model learning unit 114 can determine a machine learning model which has input learning data highly relevant to the basic learning data as the machine learning model to be learned. In this case, the basic learning data may be previously classified based on the data type, and the machine learning model may be pre-constructed for each data type. For example, the basic learning data may be previously classified according to various criteria such as place where the learning data was generated, time at which the learning data was generated, size of the learning data, a generator of the learning data, an object type within the learning data, and the like.

In addition, the model learning unit 114 can train the machine learning model by using learning algorithms including, for example, error back-propagation or gradient decent. For example, the model learning unit 114 may apply the input data to the machine learning model, thereby acquiring output label information. This process is referred to as forward propagation. In addition, the model learning unit 114 can obtain an error between the output label information and the ground truth label information, and update a weight of the machine learning model while propagating the error backwards. This process is referred to as back-propagation.

In addition, the model learning unit 114 may learn the machine learning model through supervised learning that uses, for example, the learning data as an input value. Further, for example, the model learning unit 114 may acquire the machine learning model through unsupervised learning that finds out criteria for a target task by self-learning a data type required for the target task without any supervision. In addition, the model learning unit 114 may acquire a machine learning model through semi-supervised learning or active learning. Additionally, the model learning unit 114 may learn the machine learning model, for example, through reinforcement learning that uses feedback on the correctness of a target task result obtained after learning.

Also, when the machine learning model is learned, the model learning unit 114 may store the learned machine learning model. At this time, the model learning unit 114 can store the learned machine learning model on a memory of the electronic device including the data recognition unit 120. Alternatively, the model learning unit 114 may store the learned machine learning model in a memory of a server connected to the electronic device via wired or wireless network.

A memory on which the learned machine learning model is stored may also store instructions or data related to at least one other element of the electronic device. Further, the memory may store software and/or programs. The program may include, for example, a kernel, a middleware, an application programming interface (API) and/or an application program (or "application"), and the like.

The model evaluation unit 115 can input evaluation data into the machine learning model, and make the model learning unit 114 repeat learning when a result output from the evaluation data does not satisfy predetermined criteria. At this time, the evaluation data may be predetermined data for evaluating the machine learning model.

For example, the model evaluation unit 115 may be evaluated as not satisfying the predetermined criteria if the number or ratio of evaluation data with inaccurate recognition results among the results of the learned machine learning model for the evaluation data exceeds a predetermined threshold. For example, when the predetermined criterion is defined as a ratio of 2% and the learned machine learning model outputs incorrect recognition results for evaluation data exceeding 20 among a total of 1000 evaluation data, the model evaluation unit 115 may evaluate as the learned machine learning model is inappropriate.

On the other hand, when there are multiple learned machine learning models, the model evaluation unit 115 can evaluate whether each of the learned learning model satisfies the predetermined criteria and determine a model satisfying the predetermined criteria as a final machine learning model. At this time, when a plurality of models satisfies the predetermined criteria, the model evaluation unit 115 can determine one or a predetermined number of models in the descending order of the highest evaluation score as the final machine learning model.

Meanwhile, at least one of the data acquisition unit 111, the preprocessing unit 112, the learning data selection unit 113, the model learning unit 114, and the model evaluation unit 115 in the data learning unit 110 may be manufactured in the form of at least one hardware chip and then mounted on the electronic device. For example, at least one of the data acquisition unit 111, the preprocessing unit 112, the learning data selection unit 113, the model learning unit 114, and the model evaluation unit 115 may be manufactured in the form of a dedicated hardware chip for artificial intelligence (AI) or as a part of an existing general purpose processor (e.g., CPU or application processor) or a graphic-only processor (e.g., GPU), and then may be mounted on the various electronic devices described above.

In addition, the data acquisition unit 111, the preprocessing unit 112, the learning data selection unit 113, the model learning unit 114, and the model evaluation unit 115 may be mounted on one electronic device or on different electronic devices separately. For example, some of the data acquisition unit 111, the preprocessing unit 112, the learning data selection unit 113, the model learning unit 114, and the model evaluation unit 115 may be included in the electronic device, and the rest of them may be included in the server.

In addition, at least one of the data acquisition unit 111, the preprocessing unit 112, the learning data selection unit 113, the model learning unit 114, and the model evaluation unit 115 may be implemented as a software module. When at least one of the data acquisition unit 111, the preprocessing unit 112, the learning data selection unit 113, the model learning unit 114, and the model evaluation unit 115 is implemented as a software module (or a program module including instructions), the software module may be stored on a non-transitory computer readable media. At this time, at least one software module may be provided by an operating system (OS) or by a predetermined application. Alternatively, some of at least one software module may be provided by an operating system (OS), and the rest of them may be provided by a predetermined application.

The data recognition unit 120 according to an embodiment of the present disclosure may include a data acquisition unit 121, a preprocessing unit 122, a recognition data selection unit 123, a recognition result providing unit 124 and a model update unit 125.

The data acquisition unit 121 can receive input data. The preprocessing unit 122 can preprocess the acquired input data so that the acquired input data can be used by the recognition data selection unit 123 or the recognition result providing unit 124.

The recognition data selection unit 123 can select necessary data from preprocessed data. The selected data can be provided to the recognition result providing unit 124. The recognition data selection unit 123 can select some or all of the preprocessed data according to a predetermined criterion. In addition, the recognition data selection unit 123 can select data according to the criterion predetermined by learning in the model learning unit 114.

The recognition result providing unit 124 can acquire result data by applying the selected data to the machine learning model. The machine learning model may be a machine learning model generated by the model learning unit 114. The recognition result providing unit 124 can output result data. The result data may be prediction label information corresponding to the input data. The prediction label information may be data that the target task intends to derive from the input data.

The model update unit 125 can update the machine learning model based on evaluation of a recognition result provided by the recognition result providing unit 124. For example, the model update unit 125 may make the model learning unit 114 update the machine learning model, by providing the recognition result provided by the recognition result providing unit 124 to the model learning unit 114.

Meanwhile, at least one of the data acquisition unit 121, the preprocessing unit 122, the recognition data selection unit 123, the recognition result providing unit 124, and the model update unit 125 in the data recognition unit 120 is manufactured in the form of at least one hardware chip and then mounted on the electronic device. For example, at least one of the data acquisition unit 121, the preprocessing unit 122, the recognition data selection unit 123, the recognition result providing unit 124, and the model update unit 125 is manufactured in the form of a dedicated hardware chip for artificial intelligence (AI), or manufactured as a part of an existing general-purpose processor (e.g., CPU or application processor) or a graphic-only processor (e.g., GPU) to be mounted on various electronic devices described above.

In addition, the data acquisition unit 121, the preprocessing unit 122, the recognition data selection unit 123, the recognition result providing unit 124, and the model update unit 125 may be mounted on one electronic device or different electronic devices separately. For example, some of the data acquisition unit 121, the preprocessing unit 122, the recognition data selection unit 123, the recognition result providing unit 124, and the model update unit 125 may be included in the electronic device, and the rest of them may be included in the server.

In addition, at least one of the data acquisition unit 121, the preprocessing unit 122, the recognition data selection unit 123, the recognition result providing unit 124, and the model update unit 125 may be implemented as a software module. When at least one of the data acquisition unit 121, the preprocessing unit 122, the recognition data selection unit 123, the recognition result providing unit 124, and the model update unit 125 is implemented as a software module (or a program module including instructions), the software module may be stored in a non-transitory computer readable media. In addition, in this case, at least one software module may be provided by an operating system (OS) or a predetermined application. Alternatively, some of at least one software module may be provided by an operating system (OS), and the rest of them may be provided by a predetermined application.

Hereinafter, a method and apparatus for performing machine learning on data sets sequentially by a data learning unit 110 will be described in detail.

Figure 2:
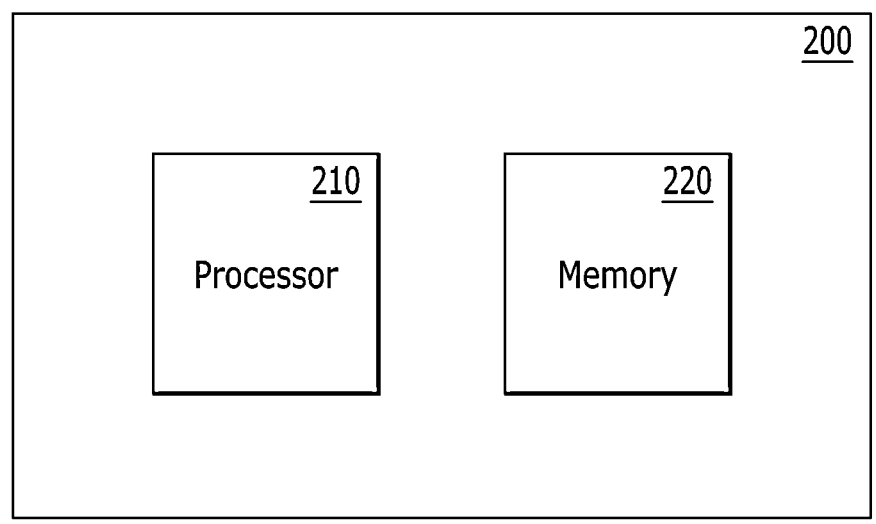
FIG. 2 is a diagram showing a medical image analysis apparatus according to an embodiment of the present disclosure.

FIG. 2 is a diagram showing a medical image analysis apparatus according to an embodiment of the present disclosure.

The medical image analysis apparatus 200 may include a processor 210 and a memory 220. The processor 210 can execute instructions stored in the memory 220.

As described above, the medical image analysis apparatus 200 may include at least one of a data learning unit 110 and a data recognition unit 120. At least one of the data learning unit 110 and the data recognition unit 120 may be implemented by the processor 210 and the memory 220.

Hereinafter, an operation of the medical image analysis apparatus 200 will be described in more detail.

Figure 3:
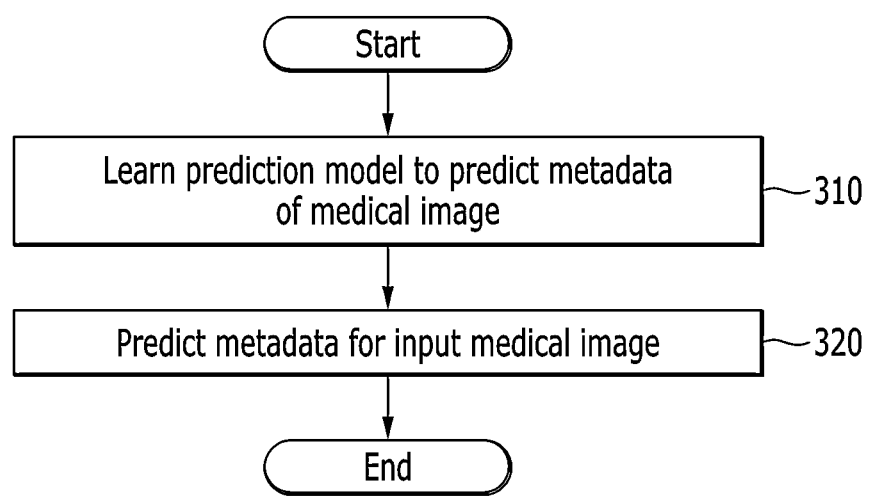
FIG. 3 is a flowchart illustrating an operation of a medical image analysis apparatus according to an embodiment of the present disclosure.

FIG. 3 is a flowchart illustrating an operation of a medical image analysis apparatus according to an embodiment of the present disclosure.

The medical image analysis apparatus 200 can execute step 310 of learning a prediction model to predict metadata of a medical image based on multiple medical images and metadata matched to each of the multiple medical images. The prediction model can be acquired by performing machine learning on a relationship between the medical image and the metadata based on a data learning unit 110 of the medical image analysis apparatus 200. The prediction model may correspond to a machine learning model shown in FIG. 1. The medical image analysis apparatus 200 can store the acquired prediction model on a memory or transmit the model to another medical image analysis apparatus 200 via wire or wireless communication.

Further, the medical image analysis apparatus 200 can execute step 320 of predicting metadata for the input medical image by using the learned prediction model. The data recognition unit 120 of the medical image analysis apparatus 200 can predict the metadata by applying the prediction model to the input medical image. The prediction model may be obtained from a memory of the medical image analysis apparatus 200 or received from another medical image analysis apparatus 200.

The multiple medical images for learning and the input medical image may be images in various formats.

For example, the multiple medical images for learning and the input medical image may be images corresponding to digital imaging and communications in medicine (DICOM) standard. According to the DICOM standard, the medical image analysis apparatus 200 may store information related to the medical image in a DICOM header.

The DICOM header may include standard data elements. The standard data elements refer to elements related to a medical image defined by the DICOM standard. The medical image analysis apparatus 200 can acquire metadata from the standard data elements. The DICOM header may include a non-standard data element. The non-standard data element is not defined by the DICOM standard, but refers to an element related to a medical image generated to suit the requirements of a medical image apparatus manufacturer or medical institution. The medical image analysis apparatus 200 can acquire metadata from the non-standard data element.

Information related to the medical image may be stored in a storage space other than the DICOM header. The medical image analysis apparatus 200 may store various information related to the medical image along with a matching relationship of medical images. Further, the medical image analysis apparatus 200 can acquire metadata based on various information related to the medical image.

Hereinafter, a process of acquiring metadata form a DICOM header will be described in more detail with reference to FIG. 4.

Figure 4:
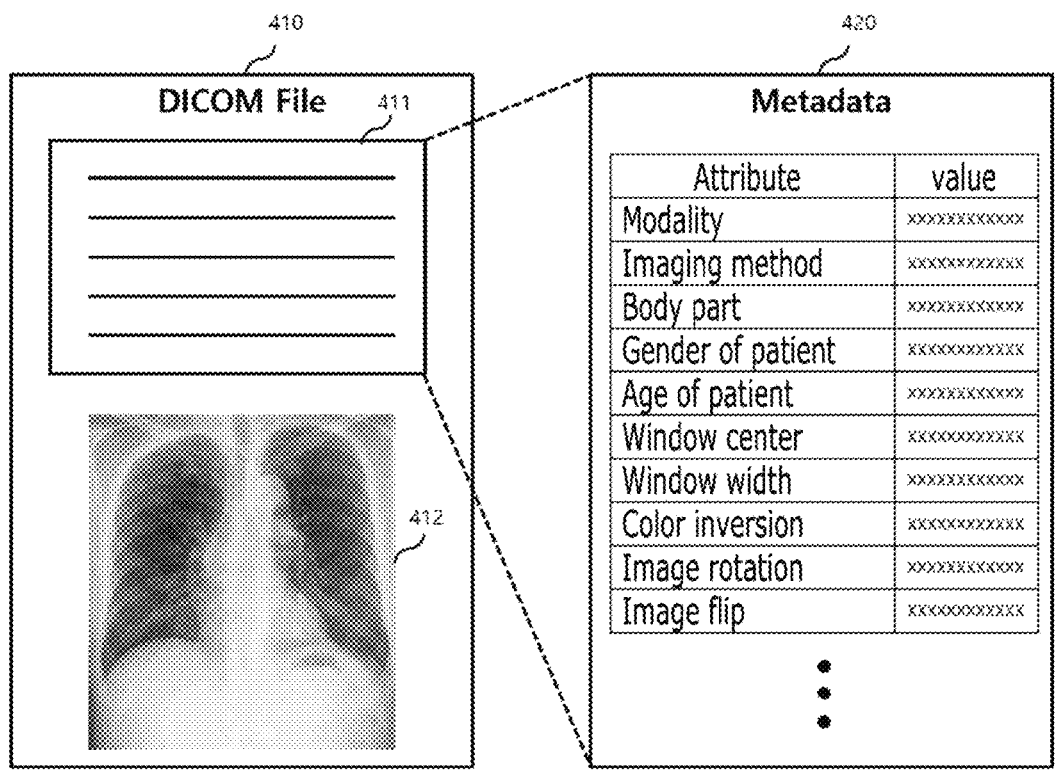
FIG. 4 is a diagram showing a structure of a DICOM file according to an embodiment of the present disclosure.

FIG. 4 is a diagram showing a structure of a DICOM file according to an embodiment of the present disclosure.

The DICOM file 410 may include a DICOM header 411 and a medical image 412. The medical image 412 may include various medical images, and may include, for example, at least one of CT, X-RAY, Mammography, and MRI images. The DICOM header 411 can include diverse information related to the medical image. The medical image analysis apparatus 200 can acquire metadata 420 based on diverse information related to the medical image 412 contained in the DICOM header 411.

The DICOM header 411 can include a standard data element or a non-standard data element. The medical image analysis apparatus 200 can acquire metadata based on the standard data element or the non-standard data element. The metadata 420 may include at least one of information related to an object included in a medical image, information on an imaging environment of a medical image, information on a type of a medical image, and information related to a display method of a medical image More specifically, the information related to the object included in the medical image may include at least one of information on body parts included in the medical image, information on existence of an artifact, and information on a patient. Here, the artifact may include at least one of an implant or a medical device. The information on the body parts included in the medical image may be expressed as an index corresponding to the body parts. For example, the information on the body parts may include at least one of indexes indicating a chest, a breast, a lung, an abdomen, an arm, or a leg.

Also, the information related to the object included in the medical image may include information on the existence of an artifact. The artifact may be inserted into the patient's body for medical or cosmetic purposes. The artifact may include at least one of an implant or a medical device. In addition, the medical device may include at least one of a tube, a catheter, or an electronic device (e.g. cardiac implantable electronic device (CIED)). The information of the existence of the artifact may be information indicating whether there is an artifact in the medical image. Since the artifact has a unique shape and texture, the medical image analysis apparatus 200 may acquire information on the existence of the artifact in the medical image based on a prediction model. The information on a patient may include gender or age information of the patient. The age information of the patient may be a numerical value representing the age of the patient. Further, the metadata may include the birthday of the patient, and the medical image analysis apparatus 200 can calculate the age information of the patient from the birthday of the patient. In addition, the age information of the patient may be information indicating an age range, for example, an age group. In an embodiment, the age information of the patient may be expressed as an index representing child, youth, middle age, or age group. Since a degree of physical development varies according to the age of the patient, a body structure shown in the medical image may be different. Here, a body shown in the medical image may be an object. The medical image analysis apparatus 200 may acquire the age information of the patient based on a structure of an object shown in the medical image. In addition, the medical image analysis apparatus 200 may acquire the age information of the patient from the medical image based on the prediction model.

Information on imaging environment of the medical image may include diverse information related to imaging of the medical image. The information on the imaging environment of the medical image may include at least one of modality information of the medical image or information on an imaging method of the medical image.

The modality information of the medical image may indicate which type of imaging equipment was used to take the medical images. For example, the modality information of the medical image may be an index to indicate that the medical image 412 is any one of CT, MRI, X-ray, mammography, or ultrasonic image. However, the modality information of the medical image is not limited thereto, and may represent various medical images taken on a patient.

In addition, the information on the imaging environment of the medical image may include information on an imaging method of the medical image. The information on the imaging environment of the medical image may correspond to a predetermined index expressed as numerical numbers or letters.

The information on the imaging method of the medical image may include information on a view of imaging the object. For example, information on a view when imaging a breast as an object may include a craniocaudal (CC) view, a mediolateral oblique (MLO) view, a mediolateral (ML) view, or a lateralomedial (LM) view. Since an overall shape of the object varies depending on the view, the medical image analysis apparatus 200 can automatically acquire information on the view based on the prediction model.

Also, the object displayed in the medical image may include a chest area. Here, the information on the view may include a posterior-anterior (PA) view, an anterior-posterior (AP) view, a lateral view, an AP erect view, a supine view, a lordotic view, a lateral decubitus view, an expiratory chest radiograph view, a sternum lateral view, a sternum oblique view, a ribs AP view, a ribs PA view, and a ribs oblique view.

Hereinafter, the PA view and AP view will be described in more detail. The information on the view may include information indicating whether an X-ray was irradiated from anterior to posterior of a patient or from posterior to anterior of the patient, which is referred to as an anterior-posterior (AP) view and posterior-anterior (PA) view, respectively. In general, an X-ray is irradiated from posterior to anterior of the patient when imaging the patient while standing up. When the patient has difficulty standing up, an X-RAY is irradiated from anterior to posterior to acquire an X-ray image.

In addition, the information on the imaging method of the medical image may include magnification information. The magnification information may represent a magnification of the medical imaging device with which the medical image is taken. The information of a large magnification may represent that the object was taken with being enlarged. Also, the information of a small magnification may represent that the object was taken with being reduced.

In addition, the information on the photographing method of the medical image may include information on whether spot compression was used. The spot compression is a method for photographing in more detail by pressing a partial area of an object. According to the spot compression, by pushing a normal tissue of an object out of the way with a compression plate, the medical image acquisition device can take a more detailed and enlarged image of a lesion suspicious region. Therefore, medical workers can easily diagnose the suspicious area of the object. When a medical image is acquired using spot compression, the compression plate is included in the medical image or a specific pattern is formed on the medical image because the object was pressed. Therefore, the medical image analysis apparatus 200 can automatically acquire the information on whether spot compression was used based on the prediction model.

The information on a type of medical image may include information on a presentation intent type of the medical image. Information on the presentation intent type may indicate that the medical image is a "final image" for diagnosis by medical workers. In addition, the information on the presentation intent type may indicate that the image is an "image for processing" that requires input from medical workers or additional processing to acquire the final image. The image for processing may be an intermediate medical image that can be displayed before the final medical image is acquired. Information related to a display method of a medical image may include at least one of window center information of a medical image, window width information, color inversion information, image rotation information, and image flip information.

The window center information and window width information will be described with reference to FIG. 5.

FIG. 5 shows CT information based on window center information and window width information according to an embodiment of the present disclosure.

The window center information and window width information may be information for adjusting brightness and contrast of a medical image.

A window graph can be drawn based on window center information 531 and window width information 532. Horizontal axis of the window graph may represent a value of an input pixel. The input pixel refers to a pixel contained in the input medical image. The value of the input pixel may have a minimum value and a maximum value. The minimum value and maximum value may be determined by at least one of an imaging device, an image display device, or image encoding and decoding standards. When the input pixel value has the maximum value, it can be indicated that the input pixel is the brightest pixel, and when the input pixel value has the minimum value, it can be indicated that the input pixel is the darkest pixel. However, the indication of the input pixel value is not limited thereto.

A vertical axis of the window graph can represent output pixel values. The medical image analysis apparatus 200 can determine output pixel values by processing the input pixel values. The medical image analysis apparatus 200 can show a medical image on a display based on the output pixel values.

For example, when the window center information 531 is "a" and the window width information 532 is "b", a window graph 521 can be generated. The medical image analysis apparatus 200 can generate a CT image 511 based on the window center information 531 and the window width information 532. The medical image analysis apparatus 200 can generate the CT image 511 by indicating an input pixel value less than a first threshold as a minimum pixel value and indicating an input pixel value greater than a second threshold as a maximum pixel value, based on the window center information 531 and the window width information 532. That is, the medical image analysis apparatus 200 can express an input pixel value greater than or equal to the first threshold value separately from an input pixel value less than or equal to the second threshold value.

An input pixel value smaller than the first threshold or an input pixel value greater than the second threshold may be a clutter signal unimportant for medical image analysis. The medical image analysis apparatus 200 can adjust the first threshold value and the second threshold value based on the window center information 531 and the window width information 532, and display pixels important for medical image analysis only.

In addition, for example, when the window center information 531 is "a" and the window width information 532 is "c", a window graph 522 can be generated as shown in FIG. 5. The medical image analysis apparatus 200 may generate a CT image 512 based on the window center information 531 and the window width information 532. The medical image analysis apparatus 200 can generate the CT image 512 by separately expressing all input pixel values based on the window center information 531 or the window width information 532.

The medical image analysis apparatus 200 can brighten more or darken more a bright part of an input pixel based on a slope of the window graph 522. The medical image analysis apparatus 200 can adjust the brightness of a medical image based on the window center information 531 or the window width information 532. For example, comparing a case where the window width information 532 is "c" with a case where the window width information 532 is "b", it can be seen that the CT image 512 is darker than the CT image 511.

When compared with the CT image 511, the CT image 512 contains all pixel values, thereby losing no information. However, since all clutter signals unimportant for medical image analysis are displayed, the CT image 512 may not be optimized for image analysis. The medical image analysis apparatus 200 can optimize the medical image for image analysis by adjusting the window center information 531 or the window width information 532.

Further, for example, when the window center information 531 is "d" and the window width information 532 is "c", a window graph 523 may be generated as shown in FIG. 5. The medical image analysis apparatus 200 can generate the CT image 513 based on the window center information 531 and the window width information 532. The medical image analysis apparatus 200 can generate the CT image 513 by brightening all input pixel values greater than a third threshold value based on the window center information 531 or the window width information 532.

The medical image analysis apparatus 200 can brighten more or darken more a bright part of an input pixel based on a slope of the window graph 522. The medical image analysis apparatus 200 can adjust the brightness of the medical image based on the window center information 531 or the window width information 532. For example, comparing a case where the window width information 532 is "a" with a case where the window width information 532 is "d", it can be seen that the CT image 512 is darker than the CT image 513.

An input pixel value greater than the third threshold value may be a clutter signal unimportant for medical image analysis. The medical image analysis apparatus 200 can display only pixels important for medical image analysis by adjusting the third threshold value, based on the window center information 531 and the window width information 532.

The medical image analysis apparatus 200 may normalize original images from various environments based on the window center information 531 or the window width information 532. The preprocessing unit 112 and the preprocessing unit 122 of the medical image analysis apparatus 200 can generate a normalized medical image from the original medical image. Also, the medical image analysis apparatus 200 can provide the prediction model to another medical image analysis apparatus. Another medical image analysis apparatus can correct the medical image based on the prediction model of the present disclosure before performing other machine learning.

Referring to FIG. 4 again, the information related to the display method of the medical image can include color inversion information. The medical image analysis apparatus 200 can invert the color of the medical image based on the color inversion information. When the color inversion information indicates inversion of the color, the medical image analysis apparatus 200 can display a medical image using a pixel value obtained by subtracting a pixel value in the medical image from a maximum pixel value that the pixel values can have.

The information related to the display method of the medical image can include information related to image rotation. The information related to image rotation can indicate the size of clockwise rotation or counterclockwise rotation of the photographed medical image information. The information related to image rotation may be expressed as an index corresponding to the rotation size or as a number in the unit of radian or degree. The medical image analysis apparatus 200 may display a rotated medical image based on the information related to image rotation.

The information related to the display method of the medical image can include image flip information. The image flip information may represent displaying the medical image with being flipped by inverting left and right on a vertical axis. However, the present disclosure is not limited thereto, and the image inversion information may represent displaying the medical image with being flipped by inverting up and down on a horizontal axis.

It has been described that the metadata 420 includes information related to at least one of information related to an object included in a medical image, information on an imaging environment of a medical image, and information related to a display method of a medical image.

As described above, the medical image analysis apparatus 200 may acquire metadata based on information stored on the DICOM header in the standard format. In addition, the medical image analysis apparatus 200 may acquire the metadata based on information stored on the DICOM header in a non-standard format. Further, the medical image analysis apparatus 200 may acquire metadata based on information stored on a storage space other than the DICOM header in the non-standard format.

The medical imaging device manufacturers or hospital may use different non-standard format. When the metadata is acquired from information stored in the non-standard format, the medical image analysis apparatus 200 should acquire metadata using different methods for different manufacturers or hospitals providing the medical image, thereby experiencing inconvenience.

A medical image analysis apparatus 200 according to the present disclosure can generate metadata based on a medical image 412 when metadata is acquired based on information stored in a non-standard format or even when there is no information related to the medical image. Step 310 of learning a prediction model of FIG. 3 will be described in detail with reference to FIG. 6 and FIG. 7.

Figure 6:
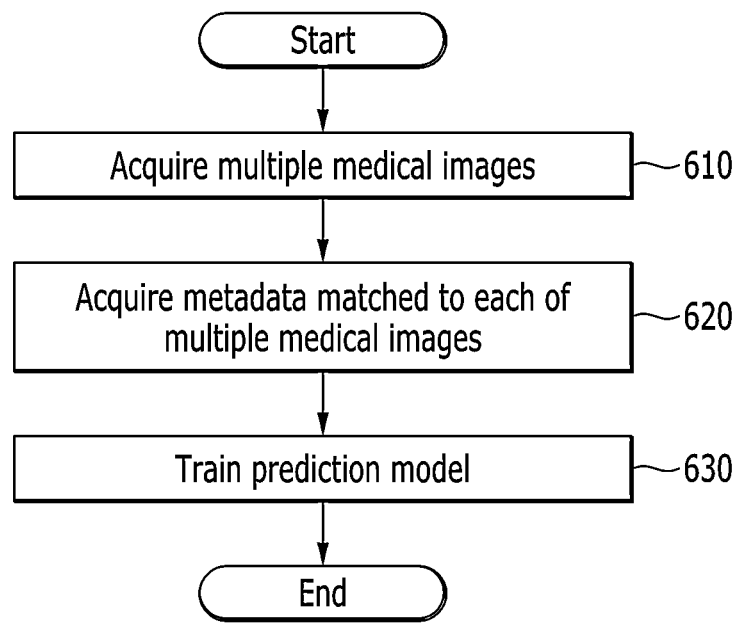
FIG. 6 is a flowchart showing an operation of a medical image analysis apparatus according to an embodiment of the present disclosure.
Figure 7:
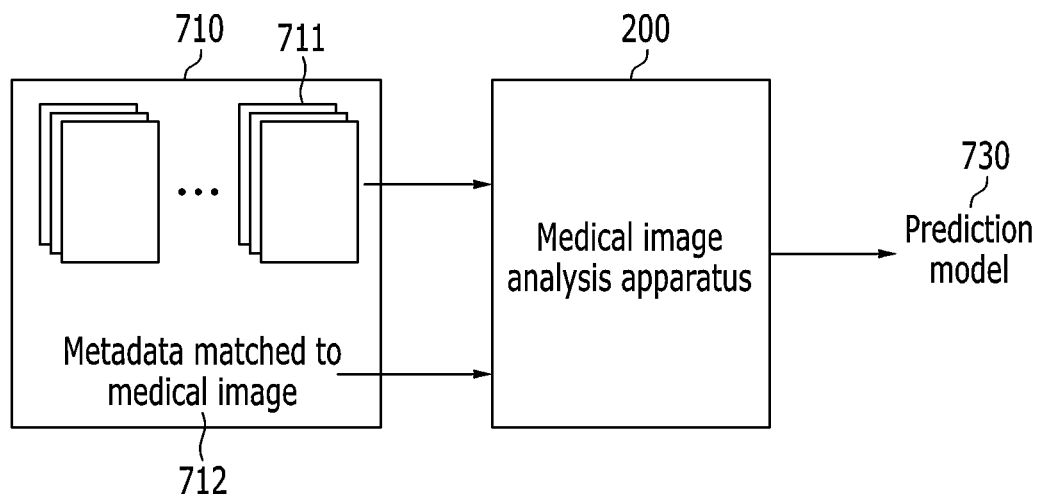
FIG. 7 is a diagram illustrating a learning process of a prediction model according to an embodiment of the present disclosure.

FIG. 6 is a flowchart showing an operation of a medical image analysis apparatus according to an embodiment of the present disclosure. In addition, FIG. 7 is a diagram illustrating a learning process of a prediction model according to an embodiment of the present disclosure.

As described above, the prediction model may be included in a machine learning model above-described with reference to FIG. 1. The process shown in FIG. 6 may be performed by a data learning unit 110 included in a medical image analysis apparatus 200. The medical image analysis apparatus 200 can receive an input data set 710 to learn a prediction model. The input data set 710 may include multiple medical images 711 and metadata 712.

The medical image analysis apparatus 200 can perform step 610 of acquiring multiple medical images 711. For example, the medical image analysis apparatus 200 can acquire multiple medical images from a memory 220. In addition, the medical image analysis apparatus 200 can acquire multiple medical images based on wired and wireless communication.

The medical image analysis apparatus 200 can perform step 620 of acquiring metadata 712 matched to each of the multiple medical images. The medical image analysis apparatus 200 can perform a step of acquiring multiple metadata matched to each of the multiple medical images from standard data elements of a DICOM header of each of the multiple medical images for learning. However, metadata acquisition is not limited thereto. The medical image analysis apparatus 200 may acquire metadata from a non-standard data element of the DICOM header or information in a non-standard format stored on a storage space other than the DICOM header. The metadata 712 may include at least one of information related to an object included in a medical image, information on a type of the medical image, information on an imaging environment of the medical image, and information related to a display method of the medical image.

Since detailed process is the same as described above with reference to FIG. 3 and FIG. 4, redundant explanation will be omitted.

The medical image analysis apparatus 200 can perform step 630 of training a prediction model by using multiple medical images for learning and the acquired multiple metadata. The medical image analysis apparatus 200 can perform supervised learning using an original medical image and label information. The label information may be metadata. The label information may be information on the DICOM header, information stored on an area other than the DICOM header, information input by a user, or information input by a medical worker on the original medical image. The medical image analysis apparatus 200 can perform machine learning by using regression or classification according to characteristics of the label information.

Machine learning can be used to learn the prediction model of the medical image analysis apparatus 200. Machine learning can be performed based on a neural network. For example, algorithms such as deep neural network (DNN), recurrent neural network (RNN), long short-term memory models (LSTM), bidirectional recurrent deep neural network (BRDNN), convolutional neural networks (CNN) can be used for machine learning, but the algorithms are not limited thereto.

The medical image analysis apparatus 200 can output learned result as the prediction model 730. The medical image analysis apparatus 200 can store the prediction model 730 on a memory. The medical image analysis apparatus 200 can transmit the prediction model 730 to another medical image analysis apparatus 200.

The step 310 of learning the prediction model has been described so far. Hereinafter, step 320 of predicting metadata using a prediction model will be described with reference to FIG. 8 and FIG. 9.

Figure 8:
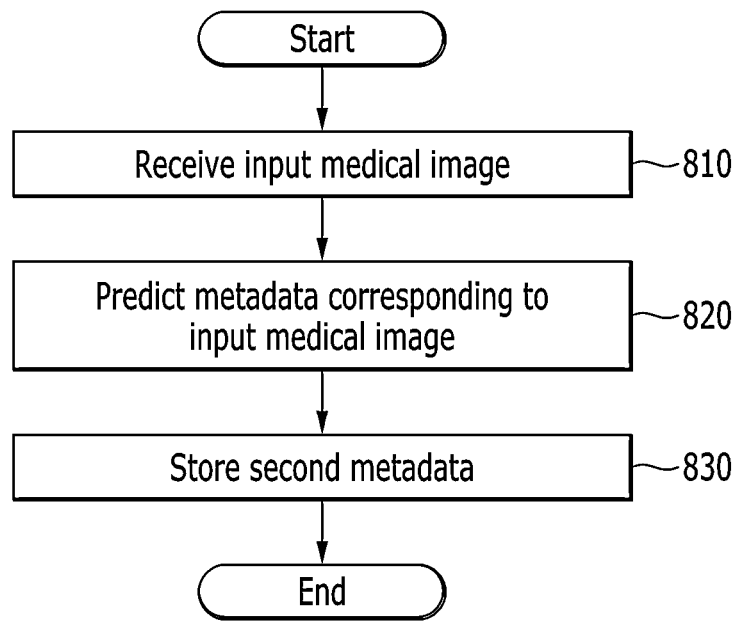
FIG. 8 is a flowchart showing an operation of the medical image analysis apparatus according to an embodiment of the present disclosure.
Figure 9:
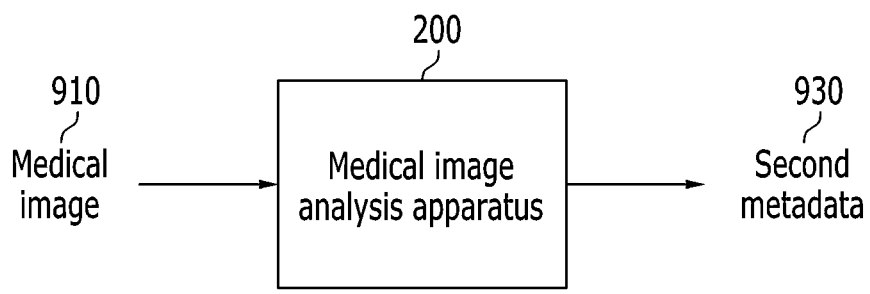
FIG. 9 is a diagram showing a process of using a prediction model according to an embodiment of the present disclosure.

FIG. 8 is a flowchart showing an operation of the medical image analysis apparatus according to an embodiment of the present disclosure. Further, FIG. 9 is a diagram showing a process of using a prediction model according to an embodiment of the present disclosure.

The process shown in FIG. 8 can be performed by a data recognition unit 120 included in a medical image analysis apparatus 200. The medical image analysis apparatus 200 may include a prediction model 730. The medical image analysis apparatus 200 may receive a prediction model from another medical image analysis apparatus 200. In addition, the medical image analysis apparatus 200 may acquire a prediction model by performing machine learning based on multiple medical images and metadata.

The medical image analysis apparatus 200 can perform step 810 of receiving a medical image 910. The medical image 910 may be an image to be analyzed by the medical image analysis apparatus 200. The medical image analysis apparatus 200 can receive the medical image 910 from a user through an input device. The medical image analysis apparatus 200 can receive the medical image 910 from another device via wired and wireless communication. The medical image 910 may be independent of multiple medical images 711. The medical image 910 may be a different image from or the same image as the multiple medical images 711.

The medical image analysis apparatus 200 can perform step 820 of predicting second metadata 930 corresponding to the input medical image 910 by using the prediction model. The second metadata 930 may include at least one of information related to an object included in the medical image 910, information on an imaging environment of the medical image, modality information of the medical image, information on a type of the medical image, and information related to a display method of the medical image 910.

As described above, the information related to the object included in the medical image may include at least one of body part information included in the medical image, information on existence of an artifact, and information on a patient. In addition, the information on the imaging method may include at least one of information on a view indicating a position from which the object is imaged, magnification information, or information on whether spot compression is used. Further, the modality information of the medical information may represent which type of imaging equipment was used for taking the medical image. Here, the information on the type of the medical image may include information on presentation intent type of the medical image. In addition, the information related to the display method of the medical image may include at least one of window center information, window width information, color inversion information, image rotation information, and image flip information.

In addition, the medical image analysis apparatus 200 can perform step 830 of matching the second metadata 930 to the input medical image 910 and storing the matched information. The medical image analysis apparatus 200 can store the second metadata 930 on a DICOM header in a standard format, but it is not limited thereto. The medical image analysis apparatus 200 can store the second metadata 930 on a DICOM header in a non-standard format, or on a storage space other than the DICOM header.

The medical image analysis apparatus 200 may store first metadata corresponding to the medical image 910. The first metadata is for the medical image 910, and may be data input by a user or data automatically generated by a medical imaging apparatus. The first metadata may be included in the medical image 910 or may be data stored corresponding to the medical image 910. Accordingly, the first metadata may be referred to as metadata stored in the medical image or metadata corresponding to the medical image.

The medical image analysis apparatus 200 can compare the first metadata with second metadata 930. The medical image analysis apparatus 200 can determine a processing method of the medical image 910 based on the comparison. The processing method will be described in more detail with reference to FIG. 11.

The medical image analysis apparatus 200 can adjust an input medical image to an optimal condition or an optimal state for performing a target task. For example, the medical image analysis apparatus 200 can perform an additional step of adjusting the input medical image based on the second metadata 930 in order to detect an abnormality in the input medical image. In addition, the medical image analysis apparatus 200 can perform a step of adjusting at least one of window center, window width, color, and an output direction of the input medical image based on the second metadata 930.

For example, the second metadata 930 may include at least one of predicted window center information, predicted window width information, predicted color inversion information, predicted image rotation information, and predicted image flip information. The medical image analysis apparatus 200 can adjust the window center or window width of the medical image 910 based on the predicted window center information or the predicted window width information. In addition, the medical image analysis apparatus 200 can adjust the color of the medical image 910 based on the predicted color inversion information. Further, the medical image analysis apparatus 200 can determine an output direction of the medical image 910 based on the predicted image rotation information and the predicted image flip information.

The medical image analysis apparatus 200 can predict necessary metadata from an original medical image before reading a lesion from the medical image. Further, the medical image analysis apparatus 200 can adjust the medical image to be readable using the predicted value. In addition, it can be determined whether the medical image is an image to be read based on the predicted value. Accordingly, the medical image analysis apparatus 200 can provide a consistent reading result without relying on a subjective and variable DICOM header.

Figure 10:
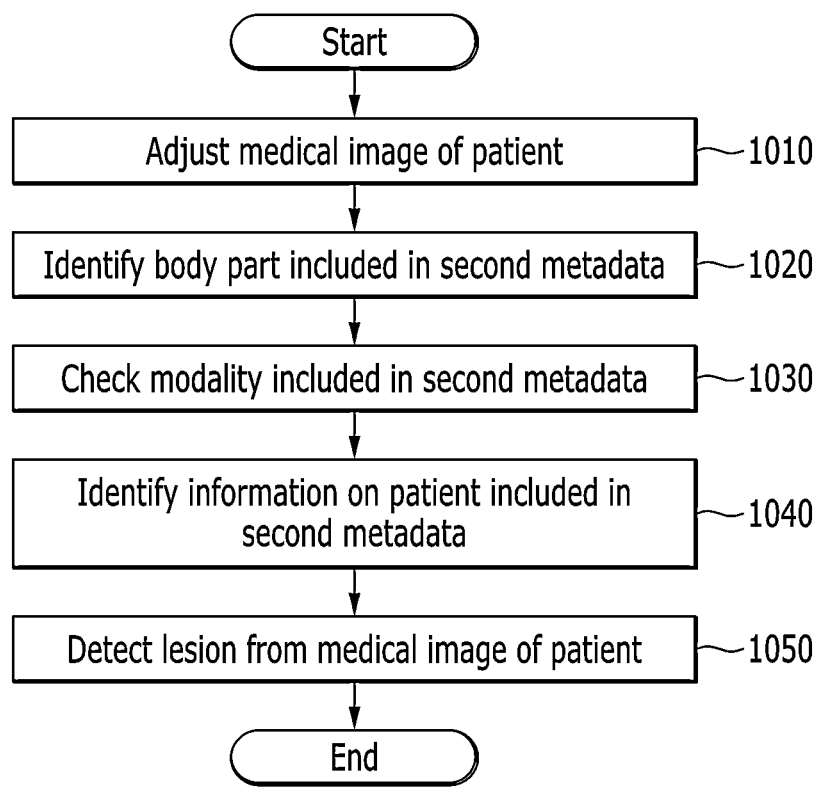
FIG. 10 is a flowchart showing a process of detecting a lesion according to an embodiment of the present disclosure.

FIG. 10 is a flowchart showing a process of detecting a lesion according to an embodiment of the present disclosure.

The medical image analysis apparatus 200 can receive a medical image of a patient. As described above with reference to FIG. 8, the medical image analysis apparatus 200 can predict metadata by applying a prediction model to the medical image of a patient. Since the metadata is predicted based on the same prediction model, the medical image analysis apparatus 200 can acquire the second metadata 930 based on the same criterion no matter which medical image is received. Therefore, the medical image analysis apparatus 200 can increase a success rate of a target task by applying the machine learning model to at least one of the medical image and the metadata. The target task may be lesion detection.

In order to detect abnormality in the input medical image, the medical image analysis apparatus 200 can perform step 1010 of adjusting the medical image of the patient based on the second metadata 930. In addition, the medical image analysis apparatus 200 can perform a step of adjusting at least one of window center, window width, color, and an output direction of the input medical image based on the second metadata.

The medical image analysis apparatus 200 can perform step 1020 of identifying a body part included in the second metadata 930. The medical image analysis apparatus 200 can check whether the body part information of the second metadata 930 matches with the body part for which an abnormality is to be detected.

For example, when a user diagnoses an abnormality from the medical image of the patient, a medical image of a specific body part may be required. The user can input information on the specific body part into the medical image analysis apparatus 200. Alternatively, the medical image analysis apparatus 200 can automatically acquire information on the specific body part that corresponds to a lesion the user is looking for. The medical image analysis apparatus 200 can determine whether the medical image of the patient is an image corresponding to the specific body part, by comparing the information on the specific body part with the information on the body part included in the second metadata 930. When the information on the specific body part does not agree with the information on the body part included in the second metadata 930, the medical image analysis apparatus 200 can acquire a new medical image of the patient or perform an operation for acquiring a new medical image of the patient.

The medical image analysis apparatus 200 can perform step 1030 of checking modality included in the second metadata 930. The medical image analysis apparatus 200 can check whether the modality information of the second metadata 930 is suitable for detecting an abnormality.

For example, a medical image of a specific modality may be required for the user to diagnose an abnormality from the medical image of the patient. The user can input information on the specific modality into the medical image analysis apparatus 200. Alternatively, the medical image analysis apparatus 200 can automatically acquire the specific modality information required to detect a lesion the user is looking for. The medical image analysis apparatus 200 can identify whether the medical image of the patient is an image based on the specific modality, by comparing the specific modality information with modality information included in the second metadata 930. When the specific modality information does not agree with the modality information included in metadata, the medical image analysis apparatus 200 can acquire a new medical image of the patient or perform operation to acquire a new medical image of the patient.

The medical image analysis apparatus 200 can perform step 1040 of identifying information on the patient included in the second metadata. The medical image analysis apparatus 200 can check whether the information on the patient included in the second metadata is suitable for detecting an abnormality.

For example, a user may need information on a specific patient to diagnose an abnormality from the medical image of the patient. The medical image analysis apparatus 200 can determine whether a diagnosis target is the same person as a patient corresponding to the medical image. In addition, the medical image analysis apparatus 200 can diagnose on patients in a specific age range in order to diagnose abnormalities. For example, the user may input information about the patient into the medical image analysis apparatus 200. Alternatively, the medical image analysis apparatus 200 may automatically acquire patient information required for detecting a lesion the user is looking for. The medical image analysis apparatus 200 can compare the input patient information with the patient information included in metadata. When the input patient information does not agree with the patient information included in the metadata, the medical image analysis apparatus 200 may output a warning message.

The medical image analysis apparatus 200 can perform step 1050 of detecting a lesion from the medical image 910 of the patient. In order to detect a lesion from a medical image, the medical image analysis apparatus 200 can use an abnormality detection machine learning model dedicated to lesion detection.

The medical image analysis apparatus 200 may include an abnormality detection machine learning model. The medical image analysis apparatus 200 can receive an abnormality detection machine learning model from another medical image analysis apparatus 200. Alternatively, the medical image analysis apparatus 200 can acquire an abnormality detection machine learning model by performing machine learning based on multiple medical images and a lesion label corresponding to each of the multiple medical images. The medical image analysis apparatus 200 can generate a machine learning model using the data learning unit 110. Since the general process of generating a machine learning model was described with reference to FIG. 1, redundant description will be omitted.

In addition, the medical image analysis apparatus 200 can detect a lesion by applying the medical image 910 to an abnormality detection machine learning model. A data recognition unit 120 included in the medical image analysis apparatus 200 can detect information on a lesion by applying the medical image 910 to the abnormality detection machine learning model. Here, the information on the lesion may include at least one of a lesion name, a position of a lesion, and the severity of the lesion. Since the general process of performing a target task based on an abnormality detection machine learning model was described with reference to FIG. 1, redundant description will be omitted.

As described above, a process in which the medical image analysis apparatus 200 detects a lesion based on an abnormality detection machine learning model has been explained with reference to FIG. 10. However, the process is not limited thereto. Another embodiment different from the embodiment shown in FIG. 10 will be described with reference to FIG. 11. From FIG. 11, steps that are performed by the medical image analysis apparatus 200 to detect a lesion will be described. Some elements described with reference to FIG. 11 can also be used in the embodiment shown in FIG. 10.

Figure 11:
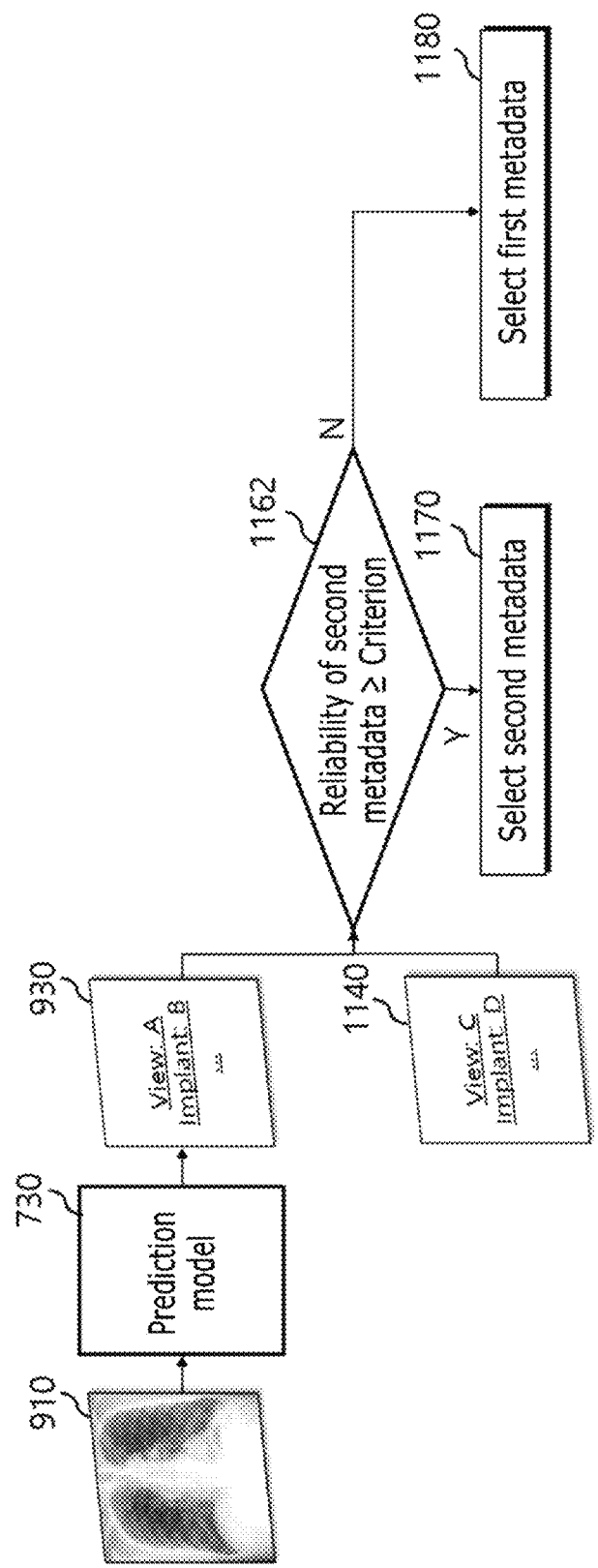
FIG. 11 is a block diagram illustrating an operation of a medical image analysis apparatus according to an embodiment of the present disclosure.
Figure 12:
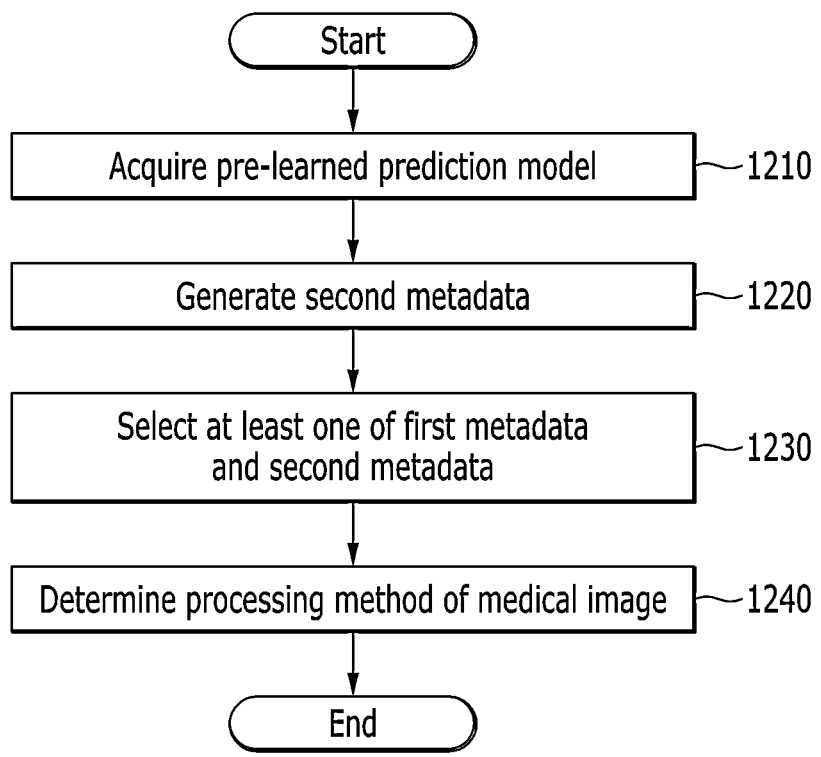
FIG. 12 is a flowchart illustrating an operation of an image analysis apparatus according to another embodiment of the present disclosure.

FIG. 11 is a block diagram illustrating an operation of a medical image analysis apparatus according to an embodiment of the present disclosure. In addition, FIG. 12 is a flowchart illustrating an operation of an image analysis apparatus according to another embodiment of the present disclosure. Hereinafter, FIG. 12 will be described along with FIG. 11.

The medical image analysis apparatus 200 can perform step 1210 of acquiring a prediction model 730 to predict metadata for a medical image from the medical image. As already described with reference to FIG. 8, the medical image analysis apparatus 200 may have stored the prediction model 730 in advance. The medical image analysis apparatus 200 can receive a prediction model from another medical image analysis apparatus 200. In addition, the medical image analysis apparatus 200 can obtain the prediction model 730 by performing machine learning based on multiple medical images and multiple metadata. Since the process of performing machine learning on the prediction model 730 has been described with reference to FIG. 6 and FIG. 7, redundant description will be omitted.

The medical image analysis apparatus 200 can perform step 1220 of generating second metadata for the medical image 910 by using the prediction model 730. The step 1220 of generating the second metadata shown in FIG. 11 corresponds to the step 820 of predicting the metadata 930 corresponding to the medical image 910 shown in FIG. 8. Thus, redundant description will be omitted.

The medical image 910 may be an image to be analyzed by the medical image analysis apparatus 200. The medical image analysis apparatus 200 can receive a medical image 910 from a user via an input device. The medical image analysis apparatus 200 can receive a medical image 910 from another device via wired and wireless communication. The medical image analysis apparatus 200 can use a pre-stored medical image 910. The medical image 910 may be independent of multiple medical images 711 used to generate the prediction model 730. The medical image 910 may be different from or the same as the multiple medical images 711 used to generate the prediction model 730.

The medical image analysis apparatus 200 can perform step 1230 of selecting at least one of first metadata 1140 and second metadata 930 corresponding to the medical image 910. The first metadata 1140 may be data corresponding to the medical image 910. The first metadata 1140 may be metadata input by a user or generated by a medical device in the process of generating the medical image 910. The first metadata 1140 may be generated by applying a different criterion to each medical image. For example, the first metadata 1140 may be generated differently even for the same medical image, due to a difference in the criteria used by medical institutions, a difference in medical imaging equipments, or the subjectivity of a user. Here, the first metadata 1140 may have missing information. This is because the user may omit inputting information or the medical device may omit inputting information based on the settings.

Meanwhile, the second metadata 930 may be data acquired based on the same prediction model 730. The second metadata 930 is information acquired from the medical image 910 according to the same criterion, and there may be no missing information.

The abnormality detection machine learning model can be a model machine-learned based on a medical image satisfying a specific condition. Therefore, the abnormality detection machine learning model can accurately predict a lesion with respect to a medical image satisfying the specific condition. The medical image analysis apparatus 200 may select a medical image that satisfies a predetermined condition by using at least one of the second metadata 930 and the first metadata 1140. In addition, when the predetermined condition is satisfied, the medical image analysis apparatus 200 can accurately predict a lesion by applying the medical image to the abnormality detection machine learning model. That is, the medical image analysis apparatus 920 can determine whether the medical image 910 is suitable to be applied to the abnormality detection machine learning model, by using at least one of the second metadata 930 and the first metadata 1140.

The first metadata 1140 and the second metadata 930 may include at least one of information related to an object included in the medical image, information on a type of the medical image, information on an imaging environment of the medical image, and information related to a display method of the medical image. Since the information related to the object included in the medical image, the information on the type of the medical image, the information on the imaging environment of the medical image, and the information related to the display method of the medical image have been described already, redundant description will be omitted.

The medical image analysis apparatus 200 can determine the selected metadata based on at least one of the first metadata 1140 and the second metadata 930. The selected metadata may be one of first metadata 1140 and second metadata 930, but is not limited thereto. Further, the selected metadata may be acquired using both the first metadata 1140 and the second metadata 930. For example, the selected metadata may be an average of the first metadata 1140 and the second metadata 930, and may be an output of a predetermined formula for the first metadata 1140 and the second metadata 930.

A method for acquiring the selected metadata by the medical image analysis apparatus 200 will be described in more detail with reference to FIG. 13.

The medical image analysis apparatus 200 can perform step 1240 of determining a processing method for the medical image 910 based on the selected metadata. As described above, the selected metadata may be acquired based on at least one of the first metadata 1140 and the second metadata 930. The medical image analysis apparatus 200 can determine a processing method of the medical image 910 based on at least one of the first metadata 1140 and the second metadata 930.

The determined processing method may be about whether to apply the medical image 910 to the abnormality detection machine learning model. For example, the medical image analysis apparatus 200 may determine whether the medical image 910 is suitable for the abnormality detection machine learning model based on the selected metadata. The medical image analysis apparatus 200 can perform a step of determining whether the selected metadata satisfies a predetermined condition. In addition, when the selected metadata satisfies the predetermined condition, the medical image analysis apparatus 200 can perform a step of applying the medical image 910 to the abnormality detection machine learning model. Here, that the selected metadata satisfies the predetermined condition may indicate that the medical image 910 is suitable for the abnormality detection machine learning model. Oppositely, when the selected metadata does not satisfy the predetermined condition, the medical image analysis apparatus 200 may not apply the medical image 910 to the abnormality detection machine learning model.

In addition, the determined processing method may be to determine a reference value for the abnormality detection machine learning model. The reference value may be a value used for a classifier. The classifier may include a decision function, and may classify the medical image into a specific class depending on whether result information of the abnormality machine learning model exceeds the reference value. The medical image analysis apparatus 200 can perform a step of determining the reference value for the abnormality detection machine learning model based on the selected metadata. The medical image analysis apparatus 200 can differently determine the reference value according to the selected metadata. Further, the medical image analysis apparatus 200 can perform a step of acquiring final result information by comparing the reference value with the result information of the abnormality detection machine learning model.

More specifically, the medical image analysis apparatus 200 can output the result information by applying the medical image 910 to an abnormality detection machine learning model. The result information may be obtained for at least one class. A class may correspond to actual label information. However, the present invention is not limited thereto, and the result information may be acquired for one class. The result information can be information related to whether a specific lesion exists in the medical image 910. For example, a case where a specific lesion exists may be classified as a first class, and a case where a specific lesion does not exist may be classified as a second class. The result information can be expressed as a numerical number. As the result information becomes larger, it may indicate that a specific lesion is more likely to exist in the medical image 910. When the result information is greater than the reference value, the medical image analysis apparatus 200 can determine that specific lesion exists in the medical image 910. Also, when the result information is smaller than the reference value, the medical image analysis apparatus 200 may determine that there is no specific lesion in the medical image 910. Here, information on whether a specific lesion exists may be final result information. Also, the final result information may be predicted label information.

However, the present invention is not limited thereto. As the result information becomes smaller, it may indicate that a specific lesion is more likely to exist in the medical image 910. When the result information is smaller than the reference value, the medical image analysis apparatus 200 may determine that a specific lesion exists in the medical image 910. In addition, when the result information is greater than the reference value, the medical image analysis apparatus 200 may determine that there is no specific lesion in the medical image 910.

In addition, the determined processing method may be about whether to put the predicted label of the abnormality detection machine learning model into the final analysis result. For example, the abnormality detection machine learning model can output at least one of the predicted label and reliability of the predicted label. The medical image analysis apparatus 200 can put the predicted label into the final analysis result when the reliability of the predicted label exceeds threshold reliability. The medical image analysis apparatus 200 can determine the threshold reliability based on at least one of the first metadata 1140 and the second metadata 930.

In addition, the determined processing method may be to select one from multiple abnormality detection machine learning models included in the medical image analysis apparatus 200. The medical image analysis apparatus 200 may include the multiple abnormality detection machine learning models. The multiple abnormality detection machine learning models can distinguish different lesions or use different medical images. The medical image analysis apparatus 200 can perform a step of selecting an abnormality detection machine learning model corresponding to the selected metadata from the multiple abnormality detection machine learning models. That is, the medical image analysis apparatus 200 can select an abnormality detection machine learning model optimized for analyzing the medical image 910 based on the selected metadata. Further, the medical image analysis apparatus 200 can apply the selected abnormality detection machine learning model to the medical image 910. The medical image analysis apparatus 200 can derive the best result by selecting an abnormality detection machine learning model suitable for the medical image 910.

A process of determining a method with which the medical image analysis apparatus 200 applies a medical image 910 to the abnormality detection machine learning model will be described in more detail with reference to FIG. 14 or FIG. 15. First, a process in which the medical image analysis apparatus 200 acquires selected metadata will be described with reference to FIG. 13.

Figure 13:
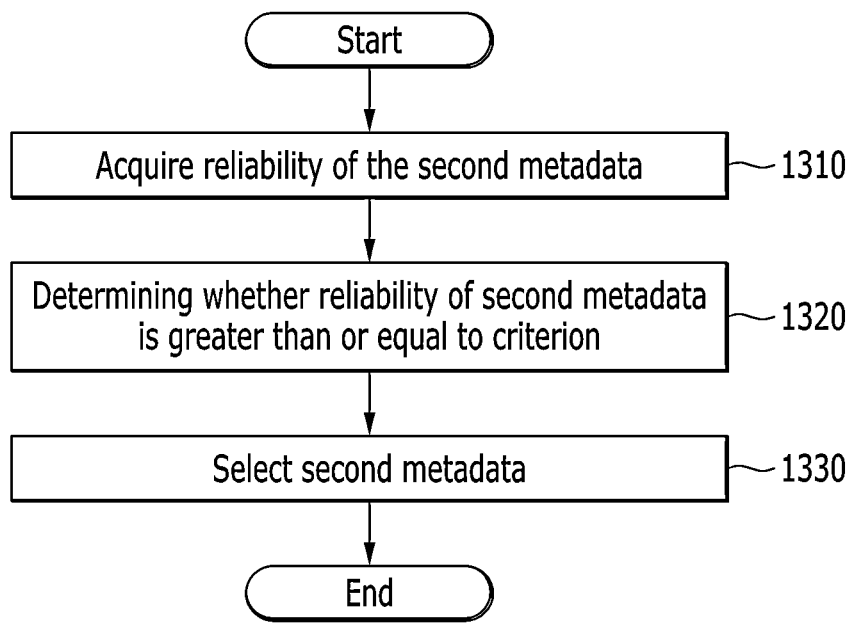
FIG. 13 is a flowchart illustrating an operation of a medical image analysis apparatus according to an embodiment of the present disclosure.

FIG. 13 is a flowchart illustrating an operation of a medical image analysis apparatus according to an embodiment of the present disclosure. The medical image analysis apparatus 200 can perform step 1220 of generating second metadata. Further, the medical image analysis apparatus 200 can perform step 1310 of acquiring reliability of the second metadata. The medical image analysis apparatus 200 can acquire at least one of the second metadata and the reliability of the second metadata based on a prediction model 730. More specifically, the medical image analysis apparatus 200 may generate at least one of the second metadata and the reliability of the second metadata by using the prediction model 730. The reliability may refer to a value related to a degree of similarity of the second metadata to ground-truth metadata or a possibility that the second metadata is the same as the ground-truth metadata. That is, the reliability can be proportional or inversely proportional to the probability that the second metadata is the same as the ground-truth metadata. The prediction model 730, being a machine learning model, can output not only the second metadata being a prediction label but also reliability corresponding thereto. The reliability may be output in various forms. For example, the reliability may be expressed as a numerical number, thereby value comparison being possible. The medical image analysis apparatus 200 can acquire reliability for each of the predicted label information. The medical image analysis apparatus 200 may classify the medical image into one of a plurality of classes related to the predicted metadata by using the prediction model. The medical image analysis apparatus 200 can acquire reliability for at least one class among the plurality of classes. However, the present invention is not limited thereto, and the medical image analysis apparatus 200 may acquire reliability for the prediction model. The medical image analysis apparatus 200 can acquire reliability of the prediction model by applying the test data set to the prediction model.

The medical image analysis apparatus 200 can perform the following steps in order to perform step 1230 of selecting at least one of the first metadata 1140 and the second metadata 930.

The medical image analysis apparatus 200 can perform step 1320 of determining whether the reliability of the second metadata is greater than or equal to a criterion. The step 1320 may correspond to step 1162 shown in FIG. 11. The criterion may be a value to determine whether the second metadata is usable. The criterion is a predetermined value and the medical image analysis apparatus 200 may have stored the criterion. The criterion may be modified by the user. The criterion may be set differently based on the type of second metadata.

When the reliability of the second metadata is greater than or equal to the criterion, the medical image analysis apparatus 200 can perform step 1330 of selecting the second metadata 930. The step 1330 may correspond to step 1170 shown in FIG. 11. The selected metadata may be the same as the second metadata 930. The medical image analysis apparatus 200 can determine a method with which the medical image 910 is applied to an abnormality detection machine learning model based on the second metadata 930.

When the reliability of the second metadata is under the criterion, the medical image analysis apparatus 200 can perform a step of selecting the first metadata 1140. That is, when the reliability of the second metadata is under the criterion, the step 1180 shown in FIG. 11 may be performed. The selected metadata may be the same as the first metadata 1140. The medical image analysis apparatus 200 can determine a method with which the medical image 910 is applied to the abnormality detection machine learning model based on the first metadata 1140.

Figure 16:
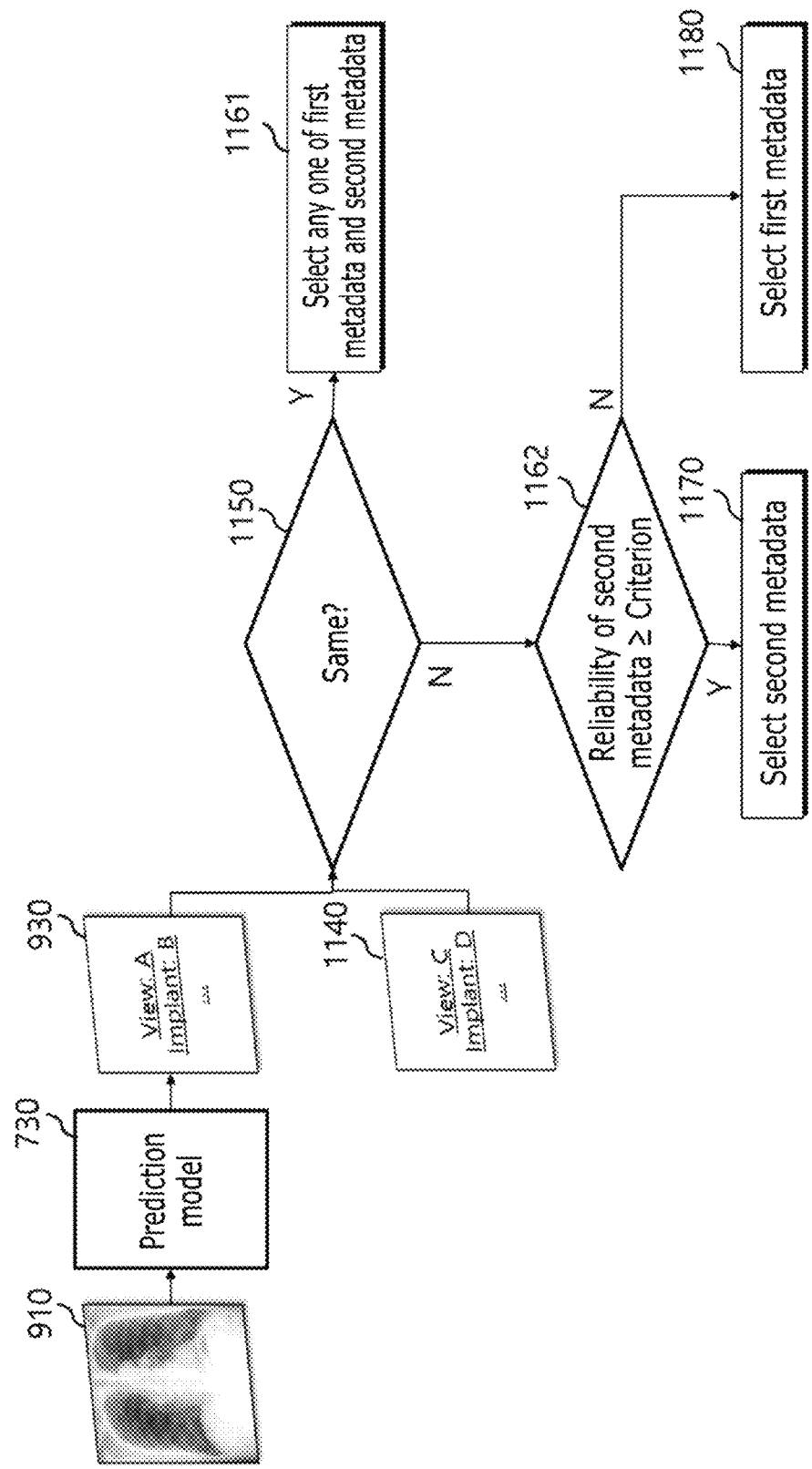
FIG. 16 is a block diagram illustrating an operation of the medical image analysis apparatus according to an embodiment of the present disclosure.

FIG. 16 is a block diagram illustrating an operation of the medical image analysis apparatus according to an embodiment of the present disclosure.

Hereinafter, steps that may be performed additionally to the steps shown in FIG. 11 will be described with reference to FIG. 16.

The medical image analysis apparatus 200 can perform a step of determining whether the first metadata 1140 is the same as the second metadata 930. This may correspond to step 1150 shown in FIG. 16. When the first metadata 1140 is the same as the second metadata 930, the medical image analysis apparatus 200 can select any one of the first metadata 1140 and the second metadata 930. Further, the medical image analysis apparatus 200 can determine a method with which a medical image 910 is applied to an abnormality detection machine learning model.

In addition, the medical image analysis apparatus 200 can perform a step of determining whether the first metadata 1140 contains information on at least one item related to the processing method. Here, at least one item related to the processing method may include information related to an object included in the medical image 910, information on an imaging method, modality information of the medical image 910, information on the type of the medical image 910, and information related to a display method of the medical image 910. For example, information may be assigned to the first metadata 1140 as a variable. First metadata may not have been assigned any value. That is, the first metadata 1140 may be a null value. At this time, the medical image analysis apparatus 200 can determine that the first metadata 1140 does not contain information on at least one item related to the processing method. When the first metadata does not contain information on at least one item related to the processing method, the medical image analysis apparatus 200 can perform a step of selecting the second metadata 930. That is, the selected metadata may be the same as the second metadata 930.

So far, the process of selecting one of the first metadata 1140 and the second metadata 930 has been described. As described above, the processing method determined by the medical image analysis apparatus 200 is about whether to apply the medical image 910 to the abnormality detection machine learning model, to determine a reference value for the abnormality detection machine learning model, or to select one from the multiple abnormality detection machine learning models included in the medical image analysis apparatus 200.

Hereinafter, a process in which a method to apply a medical image 910 to an abnormality detection machine learning model is determined based on selected metadata will be described with reference to FIG. 14 and FIG. 15.

FIG. 14 is a diagram showing a condition on which a medical image is not applied to an abnormality detection machine learning model according to an embodiment of the present disclosure.

For the convenience of explanation, a standard format of a DICOM header is exemplified, but the present disclosure is not limited thereto. The present disclosure may be implemented with a non-standard format of the DICOM header, and may be implemented with other variables even if the standard format of the DICOM header is used.

As described above, the abnormality detection machine learning model may be a model machine-learned with a medical image satisfying a specific condition. Therefore, the abnormality detection machine learning model can more accurately detect a lesion for a medical image satisfying the specific condition. The medical image analysis apparatus 200 can check whether the medical image satisfies a predetermined condition based on selected metadata. Also, the medical image analysis apparatus 200 can determine a processing method of the medical image 910 based on the selected metadata. The medical image analysis apparatus 200 can apply a medical image for which the selected metadata satisfies the predetermined condition to the abnormality detection machine learning model. Further, the medical image analysis apparatus 200 can determine a reference value for the abnormality detection machine learning model based on the selected metadata. In addition, the medical image analysis apparatus 200 may or may not put an output result of the abnormality detection machine learning model into a final result according to the condition of the medical image. Additionally, the medical image analysis apparatus 200 can select an abnormality detection machine learning model corresponding to the selected metadata from multiple abnormality detection machine learning models.

Hereinafter, the present disclosure will be described with specific examples.

Referring to a condition 1410 shown in FIG. 14, the medical image analysis apparatus 200 can perform the following process to determine a processing method of a medical image. The medical image analysis apparatus 200 can perform a step of determining whether spot compression is applied to the medical image based on information related to whether spot compression was used included in the selected metadata.

"dcm.ViewCodeSequence[0].ViewModifierCodeSequence" is information included in the selected metadata, and may be information related to whether spot compression was used. As an example of the information related to whether spot compression was used, "dcm.ViewCodeSequence[0].ViewModifierCodeSequence" is described in FIG. 14. However, the information related to whether spot compression was used may be expressed with another variable. Based on Len( ) function, the medical image analysis apparatus 200 can check whether data length of "dcm.ViewCodeSequence[0].ViewModifierCodeSequence" is not 0. When the data length is not 0, the medical image analysis apparatus 200 can determine that spot compression was used for the medical image 910.

When spot compression was used for the medical image 910, the medical image analysis apparatus 200 can perform a step of not applying the medical image 910 to the abnormality detection machine learning model. Further, when spot compression was not used for the medical image 910, the medical image analysis apparatus 200 can perform a step of applying the medical image to the abnormality detection machine learning model.

As described above, spot compression is a method of acquiring a medical image by compressing a tissue of an object. Accordingly, the shape of the tissue of the object included in the medical image may be deformed in comparison to a medical image acquired without using spot compression. It may be difficult for an abnormality detection machine learning model machine-learned based on a medical image acquired without using spot compression to accurately analyze a medical image acquired by using spot compression. Accordingly, the medical image analysis apparatus 200 may not apply the abnormality detection machine learning model to the medical image acquired by using spot compression.

Here, not to apply the abnormality detection machine learning model means only that a machine learning model not machine-learned about spot compression is not applied to a medical image for which spot compression was used. A machine learning model machined-learned about spot compression can be applied to the medical image for which spot compression was used.

The medical image analysis apparatus 200 can select an abnormality detection machine learning model corresponding to the selected metadata from multiple abnormality detection machine learning models. For example, the medical image analysis apparatus 200 can include a first abnormality detection machine learning model machine-learned based on multiple medical images acquired using spot compression and a second abnormality detection machine learning model machine-learned based on multiple medical images acquired without using spot compression. The medical image analysis apparatus 200 can determine whether spot compression is used for a medical image based on the selected metadata. The medical image analysis apparatus 200 can apply the first abnormality detection machine learning model to a medical image acquired using spot compression, and can apply the second abnormality detection machine learning model to a medical image acquired without using spot compression.

Referring to a condition 1420 shown in FIG. 14, a medical image analysis apparatus 200 can perform the following process to determine a processing method of the medical image. The medical image analysis apparatus 200 can perform a step of determining whether the medical image is an image for processing based on information on a presentation intent type contained in the selected metadata.

"dcm.PresentationIntentType" is information contained in the selected metadata, and may be information on the presentation intent type. As an example of the information on the presentation intent type, "dcm.PresentationIntentType" is described in FIG. 14. However, the information on the presentation intent type may be expressed as another variable. When the information on the presentation intent type is "FOR PROCESSING", the medical image analysis apparatus 200 can determine that the medical image is an image for processing. Additionally, when the information on the presentation intent type is not "FOR PROCESSING", the medical image analysis apparatus 200 can determine that the medical image is not an image for processing.

When the medical image is not an image for processing, the medical image analysis apparatus 200 can perform a step of applying the medical image to the abnormality detection machine learning model. Further, when the medical image is an image for processing, the medical image analysis apparatus 200 can perform a step of not applying the medical image 910 to the abnormality detection machine learning model.

As described above, the image for processing may be an intermediate medical image before acquiring a final medical image. It may be difficult for an abnormality detection machine learning model, machine-learned based on the final medical image, to accurately analyze the image for processing. Therefore, the medical image analysis apparatus 200 may not apply the abnormality detection machine learning model to the image for processing.

Here, not to apply the abnormality detection machine learning model means only that a machine learning model which was not machine-learned on a medical image for processing is not applied to a medical image. A machine learning model which was machine-learned on an image for processing can be applied to the intermediate medical image.

The medical image analysis apparatus 200 can select an abnormality detection machine learning model corresponding to the selected metadata from multiple abnormality detection machine learning models. For example, the medical image analysis apparatus 200 may acquire a first abnormality detection machine learning model machine-learned based on an image for processing. Further, the medical image analysis apparatus 200 may contain a second abnormality detection machine learning model machine-learned based on a medical image not for processing. The medical image analysis apparatus 200 can determine whether a medical image is an image for processing based on the selected metadata. The medical image analysis apparatus 200 can apply the first abnormality detection machine learning model to an image for processing, and can apply the second abnormality detection machine learning model to a medical image not for processing.

Referring to a condition 1430 of shown in FIG. 14, the medical image analysis apparatus 200 can perform the following process to determine a medical image processing method. The medical image analysis apparatus 200 can perform a step of determining whether a medical image has a predetermined view, based on information on a view included in the selected metadata.

"dcm.ViewPosition" is information included in the selected metadata and may be information on a view. In FIG. 14, "dcm.ViewCodeSequence[0].ViewModifierCodeSequence" is described as an example of the information on a view. However, the information on a view may be expressed as another variable. When the object is a breast, the information on a view may include CC, MLO, ML, or LM. Since CC, MLO, ML or LM are described above, redundant descriptions will be omitted. When the object of the medical image is a chest, the information on a view may include AP or PA.

When the medical image 910 has a predetermined view, the medical image analysis apparatus 200 can perform a step of applying the medical image to the abnormality detection machine learning model. Also, when the medical image 910 does not have a predetermined view, the medical image analysis apparatus 200 can perform a step of not applying the medical image to the abnormality detection machine learning model. The medical image analysis apparatus 200 can have stored a predetermined view. The medical image analysis apparatus 200 can set the predetermined view based on an input from a user. In addition, the medical image analysis apparatus 200 can automatically set a predetermined view depending on a type of the abnormality detection machine learning model. The predetermined view may be, for example, MLO or CC. That is, the medical image analysis apparatus 200 may not apply the abnormality detection machine learning model to the ML and LM medical images. Further, the predetermined view may be, for example, AP or PA. Namely, the medical image analysis apparatus 200 may not apply the abnormality detection machine learning model to a lateral (left lateral and right lateral) medical image.

The abnormality detection machine learning model may be a model machine-learned by using a medical image with the predetermined view. Thus, the abnormality detection machine learning model can accurately analyze a medical image with the predetermined view, and may not accurately analyze a medical image without the predetermined view. Therefore, the medical image analysis apparatus 200 may not apply the abnormality detection machine learning model to a medical image without the predetermined view.

Here, not to apply the abnormality detection machine learning model means only that a machine learning model corresponding to the predetermined view is not applied. A machine learning model corresponding to views other than the predetermined view can be applied to medical images.

The medical image analysis apparatus 200 can select an abnormality detection machine learning model corresponding to the selected metadata from multiple abnormality detection machine learning models. For example, the medical image analysis apparatus 200 can acquire a first abnormality detection machine learning model machine-learned based on multiple medical images without the predetermined view and a second abnormality detection machine learning model machine-learned based on multiple medical images with the predetermined view. The medical image analysis apparatus 200 can determine a view of the medical image based on the selected metadata. The medical image analysis apparatus 200 can apply the first abnormality detection machine learning model to a medical image without the predetermined view, and can apply the second abnormality detection machine learning model to a medical image with the predetermined view.

Referring to a condition 1440 shown in FIG. 14, the medical image analysis apparatus 200 can perform the following process to determine a medical image processing method. The medical image analysis apparatus 200 can determine whether an image magnification of the medical image is less than or equal to a threshold magnification based on magnification information included in the selected metadata.

"dcm.EstimatedRadiographicMagnificationFactor" is information included in the selected metadata and may be magnification information. In FIG. 14, "dcm.EstimatedRadiographicMagnificationFactor" is described as an example of the magnification information. However, the magnification information may be expressed as another variable. Since the magnification information has been described already, redundant description will be omitted.

When the imaging magnification of the medical image is less than or equal to the threshold magnification, the medical image analysis apparatus 200 can perform a step of applying the medical image to the abnormality detection machine learning model. Further, when the image magnification of the medical image exceeds the threshold magnification, the medical image analysis apparatus 200 can perform a step of not applying the medical image to the abnormality detection machine learning model.

The threshold magnification is a predetermined value and the medical image analysis apparatus 200 may have stored the threshold magnification. The threshold magnification can be modified by the user. The threshold magnification may be set differently depending on the type of the second metadata. The threshold magnification may be, for example, 1.0.

The abnormality detection machine learning model may be a model machine-learned using a medical image of the threshold magnification or less. That is, the abnormality detection machine learning model can accurately analyze medical images with a magnification of the threshold magnification or less, and can not accurately analyze medical images with a magnification exceeding the threshold magnification. Therefore, the medical image analysis apparatus 200 may not apply the abnormality detection machine learning model to the medical image with a magnification exceeding the threshold magnification.

Here, not to apply the abnormality detection machine learning model means only that a machine learning model corresponding to a medical image with a magnification of the threshold magnification or less is not applied to a medical image with a magnification exceeding the threshold magnification. A machine learning model machine-learned on a medical image with a magnification exceeding the threshold can be applied to medical images with a magnification exceeding the threshold.

The medical image analysis apparatus 200 can select an abnormality detection machine learning model corresponding to the selected metadata among multiple abnormality detection machine learning models. For example, the medical image analysis apparatus 200 may include a first abnormality detection machine learning model machine-learned based on multiple medical images with a magnification exceeding the threshold magnification and a second abnormality detection machine learning model machine-learned based on multiple medical images with a magnification of the threshold magnification or less. The medical image analysis apparatus 200 can determine a magnification whish was applied to the medical image based on the selected metadata. The medical image analysis apparatus 200 can apply the first abnormality detection machine learning model to a medical image with a magnification exceeding the threshold magnification and can apply the second abnormality detection machine learning model to a medical image with a magnitude of the threshold magnification or less.

Referring to a condition 1450 and a condition 1460 shown in FIG. 14, the medical image analysis apparatus 200 can perform the following process to determine a medical image processing method. The medical image analysis apparatus 200 can perform a step of determining whether the medical image was rotated based on information related to image rotation contained in the selected metadata.

"dcm.Laterality" is information included in the selected metadata and can indicate whether the medical image is about a left object or a right object. For example, when the object is a breast, that "dcm.Laterality" is "L" indicates that a left breast is displayed in the medical image, and that "dcm.Laterality" is "R" indicates that a right breast is displayed in the medical image. In addition, "dcm.ImageOrientationPatien" is information included in the selected metadata, and may be information indicating the degree of rotation. For example, a condition of "dcm.Laterality=='L' and dcm.ImageOrientationPatient[1]==−1" may indicate that the medical image displays a not-rotated left breast. Further, a condition of "dcm.Laterality=='R' and dcm.ImageOrientationPatient[1]==1" may indicate that the medical image displays a not-rotated right breast. Further, as shown in FIG. 14, a condition of "dcm.Laterality =='L' and dcm.ImageOrientationPatient[1]==1" may indicate that the medical image displays a 180-degree rotated left breast. In addition, a condition of "dcm.Laterality=='R' and dcm.ImageOrientationPatient[1]==−1" may indicate that the medical image displays a 180-degree rotated right breast.

As examples of the rotation information, "dcm.Laterality" and "dcm.ImageOrientationPatient" are described in FIG. 14. However, the rotation information may be expresses with another variable.

As described above, the medical image analysis apparatus 200 can determine whether the medical image 910 is rotated. The medical image analysis apparatus 200 can perform a step of applying the not-rotated medical image to the abnormality detection machine learning model. Additionally, the medical image analysis apparatus 200 can perform a step of not applying the rotated medical image to the abnormality detection machine learning model.

The abnormality detection machine learning model may be a model machine-learned using a not-rotated medical image. That is, the abnormality detection machine learning model can accurately analyze a not-rotated medical image and may not accurately analyze a rotated medical image. Therefore, the medical image analysis apparatus 200 may not apply the abnormality detection machine learning model to the rotated medical image.

Here, not to apply the abnormality detection machine learning model means only that a machine learning model corresponding to a not-rotated medical image is not applied to a rotated image. A machine learning model machined-learned on rotated images can be applied to the rotated medical image.

The medical image analysis apparatus 200 can select an abnormality detection machine learning model corresponding to the selected metadata from multiple abnormality detection machine learning models. For example, the medical image analysis apparatus 200 may include a first abnormality detection machine learning model machine-learned based on multiple rotated medical images and a second abnormality detection machine learning model machine-learned based on multiple not-rotated medical images. The medical image analysis apparatus 200 can determine whether the medical image was rotated based on the selected metadata. The medical image analysis apparatus 200 can apply the first abnormality detection machine learning model to a rotated medical image, and can apply the second abnormality detection machine learning model to a not-rotated medical image.

Further, the medical image analysis apparatus 200 may convert the rotated medical image and then apply the converted medical image to the abnormality detection machine learning model, instead of not applying the abnormality detection machine learning model to a rotated medical image. That is, when the medical image is rotated, the medical image analysis apparatus 200 can perform a step of converting the medical image to not-rotated status. As described above, the medical image analysis apparatus 200 can acquire the degree of rotation of the image based on the rotation information. The medical image analysis apparatus 200 can convert the medical image to not-rotated status. Also, the medical image analysis apparatus 200 can perform a step of applying the converted medical image to the abnormality detection machine learning model.

Referring to a condition 1470 shown in FIG. 14, the medical image analysis apparatus 200 can perform the following process to determine a processing method of a medical image. The medical image analysis apparatus 200 can determine whether an artifact exists in the medical image, based on information on whether an artifact exists in the selected metadata.

"dcm.BreastImplantPresent" may be information on whether an artifact exists in the selected metadata. As an example of the existence of the artifact, "dcm.BreastImplantPresent" is described in FIG. 14. However the information on the existence of the artifact may be expressed as another variable.

The medical image analysis apparatus 200 can perform a step of applying the medical image to the abnormality detection machine learning model when there is no artifact in the medical image. Further, when an artifact exists in the medical image, the medical image analysis apparatus 200 can perform a step of not applying the medical image to the abnormality detection machine learning model.

The abnormality detection machine learning model can be a model machine-learned using medical images where artifacts do not exist. That is, the abnormality detection machine learning model can accurately analyze a medical image where an artifact exist, and may not accurately analyze a medical image where an artifact does not exist. Therefore, the medical image analysis apparatus 200 may not apply the abnormality detection machine learning model to the medical image where an artifact exists.

Here, not to apply the abnormality detection machine learning model means only that a machine learning model corresponding to a medical image where an artifact does not exist is not applied to a medical image where an artifact exists. A machine learning model corresponding to a medical image where an artifact exists can be applied to the medical image where an artifact exists.

The medical image analysis apparatus 200 can select an abnormality detection machine learning model corresponding to the selected metadata from multiple abnormality detection machine learning models. For example, the medical image analysis apparatus 200 may include a first abnormality detection machine learning model machine-learned based on multiple medical images where artifacts exist and a second abnormality machine learning model machine-learned based on multiple medical images where artifact do not exist. The medical image analysis apparatus 200 can determine whether an artifact exists in the medical image based on the selected metadata. The medical image analysis apparatus 200 may apply the first abnormality detection machine learning model to a medical image where an artifact exists, and may apply the second abnormality detection machine learning model to a medical image where an artifact does not exist.

Although not described in FIG. 14, the machine learning model can determine a processing method of the medical image 910 based on various information included in the selected metadata.

For example, the medical image analysis apparatus 200 can determine a processing method of the medical image 910 based on the age of the patient contained in the selected metadata.

The medical image analysis apparatus 200 can perform the following process to determine a processing method of the medical image. The medical image analysis apparatus 200 can determine whether the age information of a patient is greater than or equal to a threshold age.

At this time, the age information of the patient contained in the selected metadata may be actual age information of the patient, but is not limited thereto. The age information of the patient may not be information on the actual age of the patient, but may be information on the development of body parts. For example, the abnormality detection machine learning model can detect abnormalities in a body part manifested in a person of an age of greater than or equal to the threshold age. Since the body part is not developed in people under the threshold age statistically, the abnormality detection machine learning model may not detect the abnormality. Accordingly, the medical image analysis apparatus 200 can acquire information on whether the corresponding body part is developed based on the selected metadata. The age of the patient may be used as an example of the information on whether the corresponding body part is developed. However, diverse information other than age may be used to determine whether the corresponding body part is developed. The medical image analysis apparatus 200 can determine whether the corresponding body part is developed, by using a prediction model described with reference to FIG. 9 and FIG. 10. In addition, the medical image analysis apparatus 200 can acquire a predicted age of a patient from a medical image by using the prediction model described with reference to FIG. 9 and FIG. 10, and can determine whether the predicted age of the patient is greater than or equal to a threshold age.

The threshold age is a predetermined value and the medical image analysis apparatus 200 may have stored the threshold age. The threshold age can be modified by a user. The threshold age may be set differently depending on a target lesion of the abnormality detection machine learning model. The threshold age may be, for example, 15 years old. Further, the threshold age may vary according to learning of the machine learning model.

When the age information of the patient contained in the selected metadata is equal to or greater than the threshold age, the medical image analysis apparatus 200 can apply the medical image to the abnormality detection machine learning model. Further, when the age information of the patient included in the selected metadata is under the threshold age, the medical image analysis apparatus 200 can apply the medical image to the abnormality detection machine learning model.

The abnormality detection machine learning model may be a model machine-learned using a medical image of a patient in an age of greater than or equal to the threshold age. That is, the abnormality detection machine learning model can accurately analyze a medical image for a patient in an age of greater than or equal to the threshold age, but may not accurately analyze a medical image for a patient under the threshold age. Therefore, the medical image analysis apparatus 200 may not apply the abnormality detection machine learning model to the medical image of a patient under the threshold age.

Here, not to apply the abnormality detection machine learning model means only that a machine learning model corresponding to a medical image of a patient in an age of greater than or equal to the threshold age is not applied to a medical image of a patient under the threshold age. A machine learning model machine-learned on a medical image of the patient under the threshold can be applied to the medical image of the patient under the threshold.

The medical image analysis apparatus 200 can select an abnormality detection machine learning model corresponding to the selected metadata from multiple abnormality detection machine learning models. For example, the medical image analysis apparatus 200 may include a first abnormality detection machine learning model machine-learned based on multiple medical images of patients under the threshold age and a second abnormality detection machine learning model machine-learned based on multiple medical images of patients in the age of greater than or equal to the threshold age. The medical image analysis apparatus 200 can determine whether the age of the patient is equal to or greater than the threshold age based on the selected metadata. The medical image analysis apparatus 200 can apply the first abnormality detection machine learning model to a medical image of a patient under the threshold age, and can apply the second abnormality detection machine learning model to a medical image of a patient in the age of greater than or equal to the threshold age.

Additionally, the medical image analysis apparatus 200 can determine a processing method of the medical image 910 based on information on a body part of a patient contained in the selected metadata.

The medical image analysis apparatus 200 can perform the following process to determine the processing method of the medical image. The medical image analysis apparatus 200 can determine whether body part information of a patient contained in the selected metadata is the same as a predetermined body part. Here, the body part information of the patient may be, for example, "BodyPartExamined" in the DICOM header.

The medical image analysis apparatus 200 may have stored the predetermined body part. The medical image analysis apparatus 200 may set the predetermined body part based on an input from a user. Further, the medical image analysis apparatus 200 may automatically set the predetermined body part according to a type of the abnormality detection machine learning model. For example, the predetermined body part may be a chest or a breast.

When the body part information of the patient contained in the selected metadata is the same as the predetermined body part, the medical image analysis apparatus 200 can perform a step of applying the medical image to the abnormality detection machine learning model. Further, when the body part information of the patient contained in the selected metadata is not the same as the predetermined body part, the medical image analysis apparatus 200 can perform a step of not applying the medical image to the abnormality detection machine learning model.

The abnormality detection machine learning model may be a model machine-learned using a medical image of the predetermined body part. That is, the abnormality detection machine learning model can accurately analyze a medical image of the predetermined body part, and may not accurately analyze a medical image of body parts other than the predetermined body part. Therefore, the medical image analysis apparatus 200 may not apply the abnormality detection machine learning model to a medical image of body parts other than the predetermined body part.

Here, not to apply the abnormality detection machine learning model means only that a machine learning model corresponding to a medical image of the predetermined body part is not applied to a medical image of body parts other than the predetermined body part. A machine learning model corresponding to a medical image of body parts other than the predetermined body part can be applied to the medical image of body parts other than the predetermined body part.

The medical image analysis apparatus 200 can select an abnormality detection machine learning model corresponding to the selected metadata from multiple abnormality detection machine learning models. For example, the medical image analysis apparatus 200 may include a first abnormality detection machine learning model machine-learned based on multiple medical images of body parts other than the predetermined body part. For example, the first abnormality detection machine learning model may be for either a knee or an abdomen. Further, the medical image analysis apparatus 200 can include a second abnormality detection machine learning model machine-learned based on multiple medical images of the predetermined body part. For example, the second abnormality detection machine learning model may be for either a chest or a breast. The medical image analysis apparatus 200 can identify a body part displayed in the medical image based on the selected metadata. The medical image analysis apparatus 200 can apply the first abnormality detection machine learning model to a medical image of body parts other than the predetermined body part, and can apply the second abnormality detection machine learning model to a medical image of the predetermined body part.

In addition, the medical image analysis apparatus 200 can determine a second threshold reliability based on the selected metadata. The medical image analysis apparatus 200 can obtain at least one of an analysis result or reliability for the analysis result, by applying a medical image to the abnormality detection machine learning model. When the reliability of the analysis result is greater than or equal to the second threshold reliability, the medical image analysis apparatus 200 can perform a step of inserting the analysis result into a final result of the abnormality detection machine learning model.

FIG. 15 is a flowchart illustrating an operation of a medical image analysis apparatus according to an embodiment of the present disclosure.

Referring to a condition 1410 shown in FIG. 14, a medical image analysis apparatus 200 can perform the following process to determine a processing method of a medical image.

The medical image analysis apparatus 200 can perform step 1510 of determining a reference value for an abnormality detection machine learning model based on selected metadata. The reference value may vary depending on the selected metadata. The medical image analysis apparatus 200 can select a reference value corresponding to the selected metadata based on a pre-stored database. In addition, the medical image analysis apparatus 200 can determine a reference value corresponding to the selected metadata based on a predetermined function. The reference value may be a value to be compared with result information output from an abnormality detection machine learning apparatus.

The medical image analysis apparatus 200 can use a reference value prediction model to determine the reference value. The reference value prediction model may correspond to a machine learning model described with reference to FIG. 1. Since a description about generation and usage of the reference value prediction model is similar to the description with reference to FIG. 6 or FIG. 8, redundant description will be omitted. A target task of the reference value prediction model may be to determine a reference value corresponding to the selected metadata. At least one of information included in the selected metadata may be applied to the reference value prediction model to automatically generate the reference value. More specifically, the selected metadata may include at least one of information related to an object included in a medical image, information on an imaging environment of the medical image, information on a type of the medical image, and information related to a display method of the medical image. Such information may be input into the reference value prediction model, and the reference value prediction model may generate a predicted reference value in response.

The medical image analysis apparatus 200 can acquire result information by applying the medical image to the abnormality detection machine learning model. The abnormality detection machine learning model can output the result information. The result information may be information related to at least one lesion included in the medical image. The result information may be information related to whether a specific lesion exists in the medical image 910. The result information may be expressed as numerical numbers. As the result information becomes larger, it may indicate that a specific lesion is more likely to exist in the medical image 910. The medical image analysis apparatus 200 can compare the result information with the reference value. When the result information is greater than the reference value, the medical image analysis apparatus 200 can determine that a specific lesion exists in the medical image 910. Further, when the result information is smaller than the reference value, the medical image analysis apparatus 200 can determine that a specific lesion does not exist in the medical image 910. Here, information on whether a specific lesion exists may be final result information. Here, the final result information may be predicted label information.

However, the result information is not limited thereto. The result information may include information related to at least one of a name of the lesion, a position of the lesion, or severity of the lesion.

The result information is information related to the lesion, may be an index, and may be expressed as numerical numbers. The reason that the result information is expressed as numerical numbers is as follows. The abnormality detection machine learning model is executed on a computer device. It is difficult for the computer device to machine-learn the character as it is. Therefore, the abnormality detection machine learning model may perform machine learning using information related to the lesion expressed as an index. That is, the above-described ground truth label information may be information related to a lesion expressed as an index. The index may be a Boolean or a numerical number. The abnormality detection machine learning model can perform binary classification. For example, when indicating that there is a specific lesion, the index may be "1" or "true", and when indicating that there is no specific lesion, the index may be "0" or "false". In addition, the abnormality detection machine learning model can perform multiclass classification. For example, the abnormality detection machine learning model can classify medical images into one among three or more classes. For example, in an abnormality detection machine learning model to identify a plurality of lesions, index "0" may indicate a first lesion, index "1" may indicate a second lesion, and an index "n" may indicate an (n+1)-th lesion. Here, "n" may be an integer. The present disclosure is not limited thereto, and the index may be a real number. Further, the index may be expressed as binary numbers, decimal numbers, or hexadecimal numbers.

As described above, since the abnormality detection machine learning model machine-learns information related to the lesion expressed as an index, the result information output from the abnormality detection machine learning model can be expressed as a numerical number. The result information may be a real number including positive number and negative number, but is not limited thereto. The result information may be comparable to the reference value. The result information may be information indicating a possibility that the medical image is classified into a specific class. For example, as the result information becomes higher, it may indicate that the medical image is more likely to be classified into the first class. However, the present disclosure is not limited thereto. As the result information becomes lower, it may indicate that the medical image is more likely to be classified into the first class.

The medical image analysis apparatus 200 can perform step 1520 of acquiring final result information by comparing the result information with the reference value. The final result information may indicate classification result of the medical image. The final result information may be one of multiple classes. More specifically, when the target task of the abnormality detection machine learning model is to determine whether a specific lesion exists in a medical image and the result information acquired by the medical image analysis apparatus is greater than or equal to the reference value, the final result information may indicate that the specific lesion exists in the medical image. In addition, when the result information is less than the reference value, the final result information may indicate that the specific lesion does not exist in the medical image. However, the present disclosure is not limited thereto. When the result information acquired by the medical image analysis apparatus 200 is less than the reference value, the final result information may indicate that the specific lesion exists in the medical image. In addition, when the result information is greater than or equal to the reference value, the final result information may indicate that the specific lesion does not exist in the medical image.

The medical image analysis apparatus 200 can display the final result information. The user can diagnose based on the final result displayed on the medical image analysis apparatus 200.

Hereinafter, a specific example related to FIG. 15 will be described. The medical image analysis apparatus 200 can acquire information on a view based on selected metadata of a medical image 910. The medical image 910 may be an X-ray image. In addition, the information on a view may include at least one of PA view, AP view, lateral view, AP erect view, supine view, lordotic view, lateral decubitus view, expiratory chest radiograph view, sternum lateral view, sternum oblique view, ribs AP view, ribs PA view or ribs oblique view.

The medical image analysis apparatus 200 can determine a reference value based on the selected metadata. The medical image analysis apparatus 200 can set the reference value as a first value when the information on a view included in the selected metadata is AP view, and can set the reference value as a second value when the information on a view included in the selected metadata is PA view.

The medical image analysis apparatus 100 can acquire result information by applying the medical image 910 to an abnormality detection machine learning model. Here, the abnormality detection machine learning model may be an artificial intelligence model to determine, from the medical image, whether a specific lesion such as consolidation or mediastinal widening exists. The medical image analysis apparatus 200 can apply the same abnormality detection machine learning model to the medical image 910 regardless of whether the medical image has PA view or AP view. However, the present disclosure not limited thereto. The medical image analysis apparatus 200 may select an abnormality detection machine learning model based on whether the medical image 910 has PA view or AP view and apply the selected model to the medical image 910.

As described above, the result information may be related to whether the consolidation or mediastinal widening exists in the medical image and be expressed as numerical numbers. Here, as the result information becomes larger, it may indicate that a specific lesion is more likely to exist in the medical image 910.

The medical image analysis apparatus 200 can obtain final result information by comparing result information with the reference value. When the result information is equal to or greater than the reference value, the final result information from the medical image apparatus 200 may indicate that the consolidation or mediastinal widening exists in the medical image. Further, when the result information is less than the reference value, the final result information from the medical image analysis apparatus 200 may indicate that the consolidation or mediastinal widening does not exist in the medical image.

However, the present disclosure is not limited thereto. As the result information becomes smaller, it may indicate that a specific lesion is more likely to exist in the medical image 910. When the result information is equal to or greater than the reference value, the final result information from the medical image analysis apparatus 200 may indicate that consolidation or mediastinal widening does not exist in the medical image. Also, when the result information is less than the reference value, the final result information from the medical image analysis apparatus 200 can indicate that the consolidation or mediastinal widening exists in the medical image.

The AP view and PA view may have different characteristics. For example, since the heart is located in the front part of the human body, the heart can be relatively more visible in AP view. Since the abnormality detection machine learning model according to the present disclosure determines the reference value based on whether the medical image has PA view or AP view, the final result information can be derived by reflecting the characteristics of AP view and PA view. Therefore, the abnormality detection machine learning model can accurately detect a lesion. In addition, the abnormality detection machine learning model can reduce false-positive error or false-negative error.

In the above description, a configuration where the reference value is changed depending on the selected metadata and the reference value is the same regardless of the type of lesion is described. However, the present disclosure is not limited thereto, and the reference value may be different for each lesion. The medical image analysis apparatus 200 can determine the reference value based on the type of lesion. For example, the reference value for consolidation may be different from that for mediastinal widening. The medical image analysis apparatus 200 may compare result information on the existence of consolidation with a reference value for consolidation. In addition, the medical image analysis apparatus 200 can compare result information for mediastinal widening with a reference value for mediastinal widening.

Also, in the above description, consolidation or mediastinal widening exemplifies the lesion, but the type of the lesion is not limited thereto. By applying a similar method to other lesions, the medical image analysis apparatus 200 can determine the reference value and generate final result information based on the reference value.

So far, the present disclosure has been described focusing on various embodiments. It will be understood by those skilled in the art that various changes in form and details may be made therein without departing from the spirit and scope of the invention as defined by the appended claims. Therefore, the disclosed embodiments should be considered in an illustrative rather than a restrictive sense. The scope of the present invention is defined by the appended claims rather than by the foregoing description, and all differences within the scope of equivalents thereof should be construed as being included in the present invention.

Meanwhile, the above-described embodiments of the present invention can be written as a program that can be executed on a computer, and can be implemented in a general-purpose digital computer that executes the program using a computer-readable recording medium. The computer-readable recording medium includes a magnetic storage medium such as ROM, floppy disk, hard disc, and the like and an optically readable medium such as CD-ROM, DVD, and the like.

What is claimed is:

1. A medical image analysis apparatus comprising:
one or more processors; and
a memory configured to store one or more instructions that when executed by the one or more processors cause the one or more processors to execute operations, the operations comprising:
receiving a medical image;
obtaining metadata based on the medical image; and
determining, based on the metadata, whether the medical image is suitable for analysis by a machine learning model configured to detect abnormality,
wherein the determining comprises determining that the medical image is not suitable for the analysis by the machine learning model in response to information related to at least one item included in the metadata not satisfying a predetermined condition, and
wherein the operations further comprise obtaining a new medical image of a patient corresponding to the medical image, or performing an operation for obtaining the new medical image of the patient, in response to the information related to at least one item included in the metadata not satisfying the predetermined condition.

2. The apparatus of claim 1, wherein the machine learning model comprises a plurality of abnormality detection machine learning model, and
wherein the determining comprises:
selecting a selected abnormality detection machine learning model corresponding to the metadata from among the plurality of abnormality detection machine learning models; and
applying the medical image to the selected abnormality detection machine learning model.

3. The apparatus of claim 1, wherein the metadata comprises at least one of information related to an object included in the medical image, information related to an imaging environment of the medical image, information related to a type of the medical image, or information related to a display method of the medical image.

4. The apparatus of claim 3, wherein the information related to the object included in the medical image comprises at least one of information related to a body part included in the medical image, information related to presence of an artifact, or information related to a patient, and
wherein the determining comprises determining whether the information related to the object included in the medical image is suitable for the analysis by the machine learning model.

5. The apparatus of claim 3, wherein the information related to the imaging environment of the medical image comprises at least one of modality information of the medical image or information related to an imaging method of the medical image, and
wherein the determining comprises determining whether the information related to the imaging environment of the medical image is suitable for the analysis by the machine learning model.

6. The apparatus of claim 5, wherein the information related to the imaging method of the medical image comprises at least one of information related to a view from which a subject is taken, information related to a magnification at which the medical image is imaged, information related to whether spot compression is used, or information related to a presentation intent type of the medical image.

7. The apparatus of claim 1, wherein the obtaining the metadata based on the medical image comprises:
generating a first metadata predicted for the medical image using a prediction model; and
selecting, as the metadata, one of the first metadata and a second metadata stored corresponding to the medical image to obtain the metadata.

8. A medical image analysis apparatus comprising:
one or more processors; and
a memory configured to store one or more instructions that when executed by the one or more processors cause the one or more processors to execute operations, the operations comprising:
receiving a medical image;
obtaining metadata based on the medical image;
determining a reference value related to determination of a machine learning model configured to detect abnormality based on the metadata;
obtaining result information by applying the medical image to the machine learning model; and
obtaining final result information by comparing the reference value with the result information.

9. The apparatus of claim 8, wherein the obtaining the final result information comprises determining that the abnormality exists in the medical image in response to the result information being greater than the reference value.

10. The apparatus of claim 8, wherein the obtaining the final result information comprises determining that the abnormality exists in the medical image in response to the result information being less than the reference value.

11. A medical image analysis method executed by one or more processors, the method comprising:
   receiving a medical image;
   obtaining metadata based on the medical image; and
   determining, based on the metadata, whether the medical image is suitable for analysis by a machine learning model configured to detect abnormality,
   wherein the determining comprises determining that the medical image is not suitable for the analysis by the machine learning model in response to information related to at least one item included in the metadata not satisfying a predetermined condition, and
   wherein the method further comprises obtaining a new medical image of a patient corresponding to the medical image, or performing an operation for obtaining the new medical image of the patient, in response to the information related to at least one item included in the metadata not satisfying the predetermined condition.

12. A medical image analysis method executed by one or more processors, the method comprising:
   receiving a medical image;
   obtaining metadata based on the medical image;
   determining a reference value related to determination of the machine learning model configured to detect abnormality based on the metadata;
   obtaining result information by applying the medical image to the machine learning model; and
   obtaining final result information by comparing the reference value with the result information.

13. A non-transitory computer-readable medium storing one or more instructions that when executed by one or more processors cause the one or more processors to execute operations, the operations comprising:
   receiving a medical image;
   obtaining metadata based on the medical image; and
   determining, based on the metadata, whether the medical image is suitable for analysis by a machine learning model configured to detect abnormality,
   wherein the determining comprises determining that the medical image is not suitable for the analysis by the machine learning model in response to information related to at least one item included in the metadata not satisfying a predetermined condition, and
   wherein the operations further comprise obtaining a new medical image of a patient corresponding to the medical image, or performing an operation for obtaining the new medical image of the patient, in response to the information related to at least one item included in the metadata not satisfying the predetermined condition.

14. A non-transitory computer-readable medium storing one or more instructions that when executed by one or more processors cause the one or more processors to execute operations, the operations comprising:
   receiving a medical image;
   obtaining metadata based on the medical image;
   determining a reference value related to determination of a machine learning model configured to detect abnormality based on the metadata;
   obtaining result information by applying the medical image to the machine learning model; and
   obtaining final result information by comparing the reference value with the result information.

* * * * *